United States Patent [19]
Cohenford et al.

[11] Patent Number: 5,976,885
[45] Date of Patent: Nov. 2, 1999

[54] METHOD FOR THE DETECTION OF CELLULAR ABNORMALITIES USING INFRARED SPECTROSCOPIC IMAGING

[75] Inventors: Menashi A. Cohenford, West Warwick, R.I.; Prashant S. Bhandare, Arlington, Mass.; Frederick R. Cahn, Princeton, N.J.; Krishnaswamy Krishnan, Norwell, Mass.; Basil Rigas, White Plains, N.Y.

[73] Assignee: Bio-Rad Laboratories, Inc., Hercules, Calif.

[21] Appl. No.: 08/747,375

[22] Filed: Nov. 12, 1996

Related U.S. Application Data

[63] Continuation-in-part of application No. 08/558,130, Nov. 13, 1995.
[51] Int. Cl.⁶ .............................. G01N 33/48; A61B 6/00
[52] U.S. Cl. .............................. 436/63; 600/475; 436/64; 436/171
[58] Field of Search .................................. 600/473, 475, 600/476, 478; 250/339.01, 339.11, 341.1, 341.8, 461.2; 436/63, 64, 171, 172

[56] References Cited

U.S. PATENT DOCUMENTS 5,149,959  9/1992  Collins et al. ...................... 250/339.02
5,596,992  1/1997  Haaland et al. ......................... 600/473

Primary Examiner—Ruth S. Smith
Attorney, Agent, or Firm—Townsend and Townsend and Crew LLP

[57] ABSTRACT

This invention teaches a method to identify cellular abnormalities which are associated with disease states. In one aspect, the invention is a method to distinguish premalignant and malignant stages of cervical cancer from normal cervical cells. The method utilizes infrared (IR) spectra of exfoliated cervical cells which are dried on an infrared transparent matrix and scanned at the frequency range from 3000–950 $cm^{-1}$. The identification of samples is based on establishing a calibration using a representative set of spectra of normal, dysplastic and malignant specimens. During the calibration process, multivariate techniques such as Principal Component Analysis (PCA) and/or Partial Least Squares (PLS) are used. PCA and PLS reduce the data based on maximum variations between the spectra, and generate clusters in a multidimensional space representing the different populations. The utilization of Mahalinobis distances, or linear regression (e.g., Principle Component Regression on the reduced data from PCA) form the basis for the discrimination. This method is simple to use and achieves statistically reliable distinction between the following groups of cervical smears: normal (individuals with no prior history of dysplasia), dysplasia and malignant samples. Further, this invention discloses a method to obtain the IR spectrum of individual cervical cells fixed on an infrared transparent matrix and to use the spectra o the individual cells in the method described above. In an additional aspect, the invention is a method for using vibrational spectroscopic imaging to distinguish between normal and diseased cells.

5 Claims, 12 Drawing Sheets

| RANGE | 33%-52% | 16%-71% | 1%-22% | 4%-27% |
|---|---|---|---|---|
| PREDICTED SCORES, MEAN ± SEM BASED ON TOTAL OF 4 SMEARS | 0.446±0.02 | 0.445±0.08 | 0.772±0.04 | 0.741±0.065 |

N- DENOTES NORMAL SMEARS
N-D DENOTES NORMAL DYSPLASIA SMEARS
D- DENOTES DYSPLASIA SMEARS
C- DENOTES MALIGNANT SMEARS

| RANGE | 69%-87% | 22%-67% | 10%-43% | 1%-23% |
| --- | --- | --- | --- | --- |
| PREDICTED SCORES, MEAN ± SEM | 0.287±0.006 | 0.567±0.049 | 0.57±0.037 | 0.802±0.066 |
| BASED ON TOTAL OF 4 SMEARS | | * | * | |

N- DENOTES NORMAL SMEARS
N-D DENOTES NORMAL DYSPLASIA SMEARS
D- DENOTES DYSPLASIA SMEARS
C- DENOTES MALIGNANT SMEARS
*-DENOTES OVERLAP OF ONE OR MORE THAN ONE DATA POINTS

| RANGE | | 98%-100% | 45%-71% | 55%-79% | 1%-38% |
|---|---|---|---|---|---|
| PREDICTED SCORES, MEAN ± SEM | | 0.0016±0.047 | 0.422±0.056 | 0.329±0.046 | 0.783±0.09 |
| BASED ON TOTAL OF 4 SMEARS | | * | * | * | |

N- DENOTES NORMAL SMEARS
N-D DENOTES NORMAL DYSPLASIA SMEARS
D- DENOTES DYSPLASIA SMEARS
C- DENOTES MALIGNANT SMEARS
*-DENOTES OVERLAP OF ONE OR MORE THAN ONE DATA POINTS

METHOD FOR THE DETECTION OF CELLULAR ABNORMALITIES USING INFRARED SPECTROSCOPIC IMAGING

CROSS-REFERENCE TO RELATED APPLICATIONS

This application is a Continuation-in-Part of U.S. Ser. No. 08/558,130, filed Nov. 13, 1995 the disclosure of which is incorporated herein by reference.

BACKGROUND OF THE INVENTION

The detection of premalignant and malignant cells by the Papanicolaou smear (Pap smear) has greatly reduced the high mortality rate due to cervical cancer. Nevertheless, the Pap screening process is labor intensive and has remained essentially unchanged since it was first described by Papanicolaou almost 50 years ago. To perform the test, cells are exfoliated from a patient's cervix by scraping using a spatula or brush. The scraping is then smeared on a slide, and the slide is stained and microscopically examined. The microscopic examination is a tedious process, and requires a cytotechnologist to visually scrutinize all the fields within a slide to detect the often few aberrant cells in a specimen. Consequently, the detection of abnormal specimens depends on the level of a cytotechnologist's experience and workload, and also on the quality of the smear preparation.

A recent critical evaluation of the Pap smear reported that the error rates associated with the current technique can be startlingly high. For example, the reported false negative rate (sensitivity) ranges from 6% to 55% (see, Shingleton, H. M., et al., *CA Cancer J. Clin.*, 45:305–320 (1995)).

As a result of these concerns, attempts have been made to automate the Pap screening process and to standardize the staining procedure. Certain of the available automated systems have been designed to improve the diagnostic yield of the Pap smear by minimizing the content of blood, mucus and other non-diagnostic debris in the examined cervical scrapings. In spite of these changes and the resulting simplification of the sample, the diagnosis of Pap smears continues to be heavily influenced by subjective bias. Thus, efforts are currently being directed towards developing alternative means of diagnosing Pap smears which are based on objective criteria such as chemical or morphological changes in cervical cells.

A number of methods have been explored to detect cytological anomalies, including those using molecular and immunological techniques. One impetus behind the development of new molecular and immunological methods is the detection of the human papilloma virus (HPV). Certain subtypes of HPV have been linked to a high incidence of abnormal lesions, and are implicated in the etiology of cervical cancer. Although these techniques are specific and detect cervical specimens at high risk, they are currently cost prohibitive and too labor intensive.

Recently, differences have been reported in the Fourier Transform Infrared (FT-IR) spectra of 156 cervical samples, of which, by cytological screening, 136 were normal, 12 had cancer, and 8 had dysplasia (see, Wong et al., *Proc. Natl. Acad. Sci. USA*, 87:8140–8145 (1991)). This study relied on features of the mid-IR region (3000–950 $cm^{-1}$) to discriminate between the samples. The spectra of normal samples exhibited a prominent peak at 1025 $cm^{-1}$ which appears to be due to glycogen, and other less pronounced bands at 1047 $cm^{-1}$, 1082 $cm^{-1}$, 1155 $cm^{-1}$ and 1244 $cm^{-1}$. The spectra of specimens diagnosed with cancer exhibited significant changes in the intensity of the bands at 1025 $cm^{-1}$ and 1047 $cm^{-1}$, and demonstrated a peak at 970 $cm^{-1}$ which was absent in normal specimens. Samples with cancer also showed a significant shift in the normally appearing peaks at 1082 $cm^{-1}$, 1155 $cm^{-1}$ and 1244 $cm^{-1}$. The cervical specimens diagnosed cytologically as dysplasia exhibited spectra intermediate in appearance between normal and malignant. Based on these observations, Wong et al. concluded that FT-IR spectroscopy may provide a reliable and cost effective alternative for screening cervical specimens.

The FT-IR spectroscopic studies of Wong, et al. (1991) focused primarily on the differences between normal and malignant samples, and utilized only a few dysplastic specimens. More importantly, discrimination between specimens was achieved by inspection of spectra, and by visually detecting overt changes in peak intensity ratios at specified frequencies. Visual inspection as a basis of discrimination is not an ideal method of analysis. This approach lends itself to subjective bias and is frequently insensitive to small variations between spectra. In the case of malignant specimens, the spectral patterns are markedly altered compared to those of normal samples. However, the spectra of a great majority of specimens with low grade dysplasia (e.g. CIN I—cervical intraepithelial neoplasia) appear similar to spectra from normal samples and are difficult to distinguish. As a result, visual inspection is unreliable and unsuited for the analysis of cervical specimens.

The method of selecting peak intensity ratios to discriminate between spectra has its problems too. This technique identifies general shapes and patterns, and like the previous approach lacks acuity in the detection of subtle differences between spectra. Other disadvantages of this method include its inability to model for interferences that can be caused by nondiagnostic debris, and/or errors that can result from sample preparation and handling techniques. Aside from the latter, this method also fails to adequately model for baseline shifts, spectral fringes, batch to batch variations in samples and/or to account for the nonlinearities that can arise from spectroscopic instrumentation and refractive dispersion of infrared light.

More recently, others have reported a greater diversity in the spectra of specimens with dysplasia than previously reported by Wong et al. (see Morris, et al., *Gynecologic Oncology* 56:245–249 (1995)). Out of the 25 specimens that were evaluated, the spectra of 9/13 specimens with low grade dysplasia (CIN I) appeared essentially similar to the spectra of normal specimens. However, as dysplasia progressed from low to high (CIN I to CIN III), the magnitude of spectral differences between normal and dysplastic samples intensified. This difference was most apparent in specimens with high grade dysplasia (CIN III) which exhibited a characteristic peak at 972 $cm^{-1}$, and changes in intensity of bands at 1026 $cm^{-1}$ (decreased), 1081 $cm^{-1}$ (increased and shifted to higher frequency), 1156 $cm^{-1}$ (decreased and flattened), and 1240 $cm^{-1}$ (increased).

Even more recent studies focusing on the greater diversity in the spectra of specimens with dysplasia (Cohenford et al., *Mikrochemica Acta*, in press), have indicated that the extent of spectral changes could perhaps correlate with different stages of cervical abnormalities. For example, as Morris and co-workers demonstrated (*Gynecologic Oncology*, 56:245–249 (1995)), the spectra of specimens with severe dysplasia (CIN III) had an appearance which was intermediate between those of specimens which were diagnosed normal and those diagnosed as containing malignant cells. Unfortunately, the IR spectra of specimens which displayed mild dysplasia (CIN I) appeared essentially similar to the spectra of normal specimens.

The progression of dysplastic cells to malignant cells is not only well documented, but is also of fundamental importance in early diagnosis and prevention of cancer. As it is important, from a clinical point of view, to distinguish those specimens with dysplastic cells from those with only normal cells, a generally useful method using IR spectroscopy must be capable of this rather fine distinction. Quite surprisingly, the present invention provides such methods.

SUMMARY OF THE INVENTION

The present invention provides methods for the early detection and identification of a malignant or premalignant condition in an exfoliated cervical cell sample. The invention encompasses collecting and analyzing cervical cell samples by bulk IR spectroscopy, single-cell IR microspectroscopy and IR imaging coupled with pixel-by-pixel analysis. Additionally, the invention provides methods for detecting the chemical basis for changes in cells that by Pap cytology were classified as normal, or abnormal (e.g., dysplastic or malignant). In this aspect, the invention provides methods for detecting chemical changes in a sample of diseased cells by utilizing IR spectroscopy of bulk cell samples, IR microspectroscopy or IR imaging.

A first aspect of the invention provides methods for the identification of a malignant or premalignant condition in an exfoliated cervical cell sample.

The methods involve;
(a) drying an exfoliated cervical cell sample on an infrared transparent matrix to produce a dried cell sample;
(b) directing a beam of mid-infrared light at the dried cell sample, the beam of mid-infrared light having a frequency of from about 3000 to about 950 $cm^{-1}$ to produce absorption data for the dried cell sample; and
(c) comparing the absorption data for the dried cell sample with a calibration/reference set of infrared absorption data to determine whether variation in infrared absorption occurs in the dried cell sample, at at least one range of frequencies, due to the variation being characteristic of a malignant or premalignant condition. The method of comparison utilizes a partial least squares (PLS) or principal component analysis (PCA) statistical method and is based on absorption data which is underivatized and unsmoothed.

In another aspect, the invention is a method for the identification of a malignant or premalignant cervical condition in a host.

The method involves;
(a) directing a beam of infrared light through an optic fiber at cervical cells in the host, at a range of frequencies to produce absorption data for the cervical cells of the host; and
(b) comparing the absorption data for the cervical cells with a calibration/reference set of infrared absorption data to determine whether variation in infrared absorption occurs in the cervical cells, at at least one range of frequencies, due to the variation being characteristic of a malignant or premalignant condition, the comparing utilizing a partial least squares or principal component analysis statistical method and the absorption data being underivatized and unsmoothed, whereby the identification of a malignant or premalignant condition is made.

In another aspect, the invention is a method for the spectroscopic identification of women who are at a high risk for developing cervical dysplasia.

The method involves;
(a) creating a reference set of absorption spectra from cervical cells taken from women having no history of dysplasia, each of the samples having a combination of cells exhibiting at least one first spectrum pattern and at least one second spectrum pattern differing from each other in either source or pattern;
(b) producing absorption data for a cervical cell sample;
(c) comparing the absorption data with the reference spectra, whereby the identification of a high risk for dysplasia is made.

In another aspect the invention provides an infrared microspectroscopic method for detecting chemical differences between a cell sample and a reference cell sample.

The method involves:
(a) directing a beam of infrared light at individual cells in a cell sample to produce absorption data for the individual cells;
(b) comparing the absorption data from the individual cells with infrared absorption spectra acquired from at least one reference cell sample to generate comparison data;
(c) generating predicted scores for the comparison data of individual cells by utilizing multivariate analysis of the comparison data; and
(d) creating frequency distribution profiles from the predicted scores, whereby detection of chemical differences is achieved.

In a related aspect, the invention is an infrared microscopic technique for discriminating between normal, premalignant and malignant cells in a cell sample.

In yet a further aspect, the invention discloses an infrared spectroscopic imaging method for detecting chemical differences between a cell sample and a reference cell sample.

The method comprises:
(a) directing a beam of infrared light at a cell sample to produce absorption data for the cell sample;
(b) comparing the absorption data with a calibration/reference set of absorption spectra constructed by pixel-by-pixel analysis of infrared absorption spectra acquired from at least one reference cell sample to generate comparison data;
(c) generating predicted scores for the comparison data utilizing multivariate analysis of the comparison data; and
(d) creating frequency distribution profiles from the predicted scores, whereby detection of chemical differences is achieved.

In a related aspect, the invention provides an infrared imaging method for discriminating between normal, premalignant and malignant cell samples.

In preferred embodiments of the above summarized infrared microspectroscopic and FT-IR imaging techniques, the calibration/reference set of infrared absorption data is obtained from a representative set of cell samples which have been identified (by cytology, or other appropriate means) as normal and/or chemically aberrant.

In particularly preferred embodiments of each of the above summarized aspects of the invention utilizing infrared microspectroscopy and infrared imaging, the calibration/reference set of infrared absorption spectra is obtained from a representative set of cytologically determined normal, dysplastic and malignant cervical cells which were dried on an infrared transparent matrix.

It is within the scope of each of the above aspects and embodiments of the invention to subtract at least one background spectrum from either the absorption data comprising the calibration/reference set or the absorption data which is taken from a patient's cell sample. The subtracted spectrum or spectra can have a distinct and individual pattern. Alternatively, the subtracted spectrum or spectra can consist of a linear or non-linear combination of more than one spectrum differing from each other in their source, pattern or intensity.

DETAILED DESCRIPTION OF THE INVENTION

Abbreviations and Definitions

Figure 1:
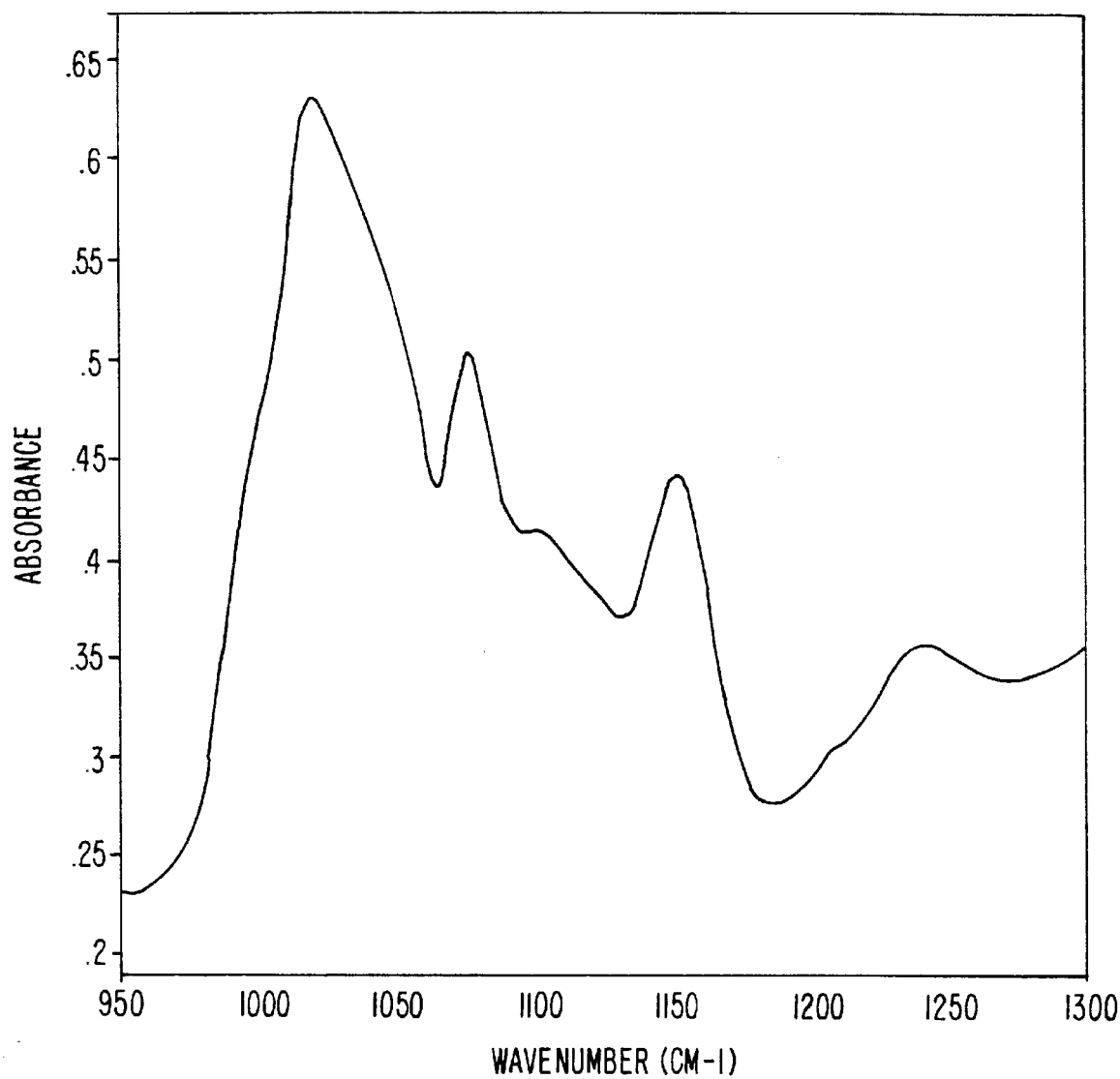
FIG. 1 shows the mid-infrared spectrum (from 950 $cm^{-1}$–1300 $cm^{-1}$) of a normal cervical scraping.

Abbreviations used herein have the following meanings: PCA, principal component analysis; PCR, principal component regression; PLS, partial least squares analysis; PRESS, prediction residual error sum of squares; FT-IR, Fourier Transform infrared spectroscopy; SPIFF, spectral image files; FPA, focal plane array; CIN, cervical intraepithelial neoplasia; HPV, human papilloma virus.

As used herein, the terms "underivatized" and "unsmoothed" are used to refer to a process whereby no arithmetic manipulations have been applied to 1) enhance the slope or changes in the slope of spectra, and 2) reduce the random noise in spectra, respectively. The term "chemical differences" refers to alterations in cellular chemistry which are associated with a disease state such as cancer. These "chemical differences" give rise to a cellular milieu which is altered from that of normal cells and this alteration is detectable by infrared spectroscopy. "Predicted scores" are generated by assigning different dummy variables to the spectra of cells falling into known categories of reference/calibration spectra (e.g., spectra associated with cells identified as normal, normal-dysplastic, dysplastic, malignant, etc.). The predicted scores indicate how closely the infrared spectra resemble the various known categories of reference/calibration spectra. "Frequency distribution profiles" are tabulations of the frequencies of the predicted scores for each biological specimen. Cell samples which are "normal" are those taken from a patient with no prior history of disease. "Normal-dysplastic cells" are those which appear normal by Pap cytology, but which are taken from patients with a history of dysplasia. The expression "infrared light" is intended to encompass energy in the infrared region of the electromagnetic spectrum. Finally, throughout this specification the terms "spectra" and "absorption data" are used interchangeably. It is understood that either of these terms can refer to the raw data generated by the spectroscopic measurement (e.g., a free induction decay (FID)), a fully processed spectrum or a spectrum which has undergone additional manipulation such smoothing or derivatization.

Description of the Embodiments

Discrimination between spectra of cervical specimens that have subtle variations requires the use of robust and sensitive methods of analysis. These methods must model for the nonlinearities that can arise due to various causes as well as account for the day to day drifts in instrument settings. Sample handling errors, spectral fringes, baseline shifts, batch to batch variations, the presence of nondiagnostic debris and all other factors that adversely affect discrimination must be also adequately accounted for and modeled. Water absorbs strongly in the mid-infrared region and contributes to changes in intensity at several frequencies. Thus, the method of analysis must also consider the varying amounts of moisture in cervical specimens. Lastly, for a method to prove robust it must distinguish between good and poor quality spectra, and exclude samples not representative of the calibration. The non-representative samples are referred to as outlier samples. An outlier sample is a sample that is statistically different from all other samples in the calibration set. In the case of cervical scrapings, an outlier spectrum can result from samples with less than an optimal number of cells, and/or specimens that are rich in blood, mucus and/or nondiagnostic debris.

In a first aspect, the present invention provides a method for the identification of a malignant or premalignant condition in an exfoliated cervical cell sample.

The method comprises:

(a) drying the exfoliated cervical cell sample on an infrared transparent matrix to produce a dried cell sample;

(b) directing a beam of mid-infrared light at the dried cell sample, the beam of mid-infrared light having a frequency of from about 3000 $cm^{-1}$ to about 950 $cm^{-1}$ to produce absorption data for the dried cell sample; and (c) comparing the infrared absorption data for the dried cell sample with a calibration/reference set of infrared absorption data to determine whether variation in infrared absorption occurs in the dried cell sample, at at least one range of frequencies, due to the variation being characteristic of the malignant or premalignant condition. The method of comparing utilizes a partial least squares (PLS) or principal component analysis (PCA) statistical method. Additionally, the absorption data is underivatized and unsmoothed.

In this method, the calibration/reference set of infrared absorption data is obtained from cell samples which have previously been identified by Pap cytology as normal, dysplastic or malignant samples. Identification of these cell types is typically made by cytological examination such as the one performed on smears. The infrared absorption spectra for each of the identified cell types is obtained for the mid-infrared region from about 3000 cm$^{-1}$ to about 950 cm$^{-1}$. Typically, the calibration/reference set of infrared absorption data is prepared from about 100 to about 1000 reference cell samples, preferably from about 100 to about 500 reference cell samples.

In general, the calibration set should be representative of all expected variations in the spectra. The infrared absorption data of all samples is then processed with a computer utilizing PCA or PLS algorithms to extract information relating to each of the variations within the calibration spectra. The resulting information is used, thereafter, to distinguish between different groups of cervical specimens (e.g. normal, dysplastic or malignant).

The exfoliated cervical cell sample is collected by standard methods such as those used in collecting samples for Pap screening and applied to an infrared transparent matrix. A variety of matrices are available for use in the present invention. Preferred matrices for mid-infrared studies are BaF$_2$, ZnS, polyethylene film, CsI, KCl, KBr, CaF$_2$, NaCl and ZnSe. A particularly preferred matrix is ZnS. Once the sample is applied to the matrix, the sample is dried to remove moisture which interferes with the infrared spectra. The methods used for drying will typically involve air-drying at ambient temperatures. Alternatively, the sample can be dried with controlled gentle heating, and by passing a stream of air or inert gas over the sample. For example, matrices with applied samples can be placed at 30° C. to 35° C. (e.g., a hot plate with temperature control knob to about 30–35° C.) and an atmosphere of, for example, air, nitrogen or argon can be passed over the samples to expedite their drying.

Others have utilized a sample holder described in U.S. Pat. No. 4,980,551. Briefly, that device is made to accommodate a set of IR transparent windows in face to face contact, and contains the means to secure the windows in the path of an infrared light beam transmitting passage. The exterior of at least one of the windows has a surface portion contoured to provide between the windows a space for the sample. This sample space being shaped to provide adjacent beam paths of different length minimizes optical interference fringes, and enhances the quality of spectra. To utilize the holder, contents from cervical scraping are first deposited in the sample space of one of the windows. With the other window carefully positioned over the specimen, the holder is tightened to secure the windows. Infrared light is passed through the sample space and the absorption of the cervical sample is recorded. Acquisition of spectra of cervical specimens by this technique is a difficult and time consuming process. For example, it is not only required that special windows be made, but also the biological specimen must remain undisturbed while being compressed between two windows. Compression frequently causes the leakage of tissue fluids, and ultimately the spilling of cervical specimens beyond the confines of the windows. Moreover, because cervical specimens can be contaminated with infectious agents such as the AIDS, Herpes and/or the various Hepatitis viruses, any leakage creates serious biological safety concerns. Still further, tissue fluids also absorb strongly in the mid-infrared region and contribute to changes in intensity at several frequencies.

In contrast, the methods of the present invention result in samples that are easy to manipulate and which provide high quality spectra. More importantly, drying eliminates the problems associated with tissue fluids, and reduces the risk of contamination by infectious agents. In a study of more than 100 cervical scrapings processed by this method, the direct deposition and drying of specimens was found to provide spectra with minimal or no fringes.

Clumping of cells in a cervical smear is generally problematic and complicates the diagnosis. A thorough dispersion of the cervical scraping causes the separation of cells from surrounding nondiagnostic debris and mucus, provides a relatively uniform suspension of cells for spectral acquisition, and enhances the possibility of detecting the abnormal cells.

Thus, in some embodiments, the samples will be dispersed prior to their application to the infrared matrix. Dispersion of the cell sample is preferably carried out in a preservative solution which maintains the integrity of the exfoliated cells. The selection criteria for a preservative solution also necessitate that the preservative solution evaporates readily, and upon evaporation, leaves no residues that create interference in the infrared spectra of cervical scrapings. An example of one such preservative solution is PRESERV CYT® (CYTYC Corporation, Marlborough, Mass., U.S.A.). Following dispersion of the cell sample, the mixture is filtered to remove the nondiagnostic debris and the solution of cells is applied in a uniform layer to an infrared matrix, as described above, and dried.

Once the sample has been prepared (and dried) on the infrared matrix, a beam of mid-infrared light is directed at the sample and the absorption of the sample is monitored using any of a number of commercially available infrared spectrophotometers. Preferably, the spectrometer is a Bio-Rad Digilab FTS 165 spectrometer equipped with a DTGS detector. Other suitable spectrometers are known to those of skill in the art. Spectra are collected at a resolution of from about 2 cm$^{-1}$ to about 10 cm$^{-1}$, preferably from about 4 cm$^{-1}$ to about 8 cm$^{-1}$. Additionally, a number of scans are taken and co-added. Preferably about 50–500 scans are co-added, more preferably about 100–300 scans are co-added. In preferred embodiments, the spectra are normalized by setting the minimum absorbance at 0.0 and the maximum absorbance at 1.0 in the frequency regions between 3000 cm$^{-1}$ to 1000 cm$^{-1}$.

After collection of the infrared absorption data for the dried cell sample, the data is compared to the calibration/reference set to determine if variations exist in the spectra which are characteristic of a malignant or premalignant condition. A number of means of performing this comparison can be used. In preferred aspects of the present invention, multivariate analysis is used.

Multivariate analysis has been used to analyze biological samples and is a promising method for analyzing spectra from cervical smears. For example, Robinson, et al. in U.S. Pat. No. 4,975,581 ( issued Dec. 4, 1990) describe a quantitative method to determine the similarities of a biological analyte in known biological fluids using multivariate analysis. In contrast to the instant invention, Robinson, et al. focuses on the in vivo evaluation of analytes in fluids, and uses noninvasive techniques. No accommodations are made to discriminate between solid biological material such as mammalian cells or to address the issues that can arise while discriminating the IR spectra of solid biological materials with varied path lengths outside the body.

Principal Component Analysis (PCA) and discriminate analysis has recently been employed to distinguish between normal and abnormal cervical scrapings. See, Zhengfang, et al., *Applied Spectroscopy* 49:432–436 (1995). However, the methods described therein did not focus on the detection of premalignant stages of cervical cancer nor did it rely on the removal of interfering and nondiagnostic material from the cervical specimens. Further, Zhengfang, et al. also relied on preprocessing algorithms that smoothed the spectra. Smoothing of spectra can obscure the subtle differences which exist between spectral patterns, and consequently can affect the discriminate analysis.

Although PCR and PLS have been used in various fields of science and in many types of applications, these techniques have never been used to discriminate in the mid-infrared region of the spectra, cervical scrapings from normal patients and patients with dysplasia or cervical cancer. Both PCR and PLS can reduce massive amounts of data into sets that can be readily managed for analysis. More importantly, when these methods are used to evaluate the spectra of mammalian cells, the techniques analyze entire regions of a spectrum and allow discrimination between the spectra of different groups of specimens.

In the first aspect of the present invention, IR spectroscopy of bulk cell samples, the comparison of the absorption data is typically carried out by a partial least squares (PLS) or principal component analysis (PCA) statistical method on data which is preferentially unsmoothed and underivatized. In the aspects utilizing infrared microspectroscopy or infrared imaging, however, the data may be smoothed and/or derivatized prior to analysis if this is deemed desirable. Preferably, comparisons using principle component regression (PCR) are carried out using PCA. A number of computer programs are available which carry out these statistical methods, including PCR-32® (from Bio-Rad, Cambridge, Mass., U.S.A.) and PLS-PLUS® and DISCRIMINATE® (from Galactic Industries, Salem, N.H., U.S.A.). Discussions of the underlying theory and calculations can be found in, for example, Haaland, et al., *Anal. Chem.* 60:1193–1202 (1988); Cahn, et al., *Applied Spectroscopy,* 42:865–872 (1988); and Martens, et al., MULTIVARIATE CALIBRATION, John Wiley and Sons, New York, N.Y. (1989). Both PCR and PLS use a library of spectra, acquired under the same conditions, from reference materials to create a reference/calibration set. These spectra are acquired under the same experimental conditions. These techniques consist of spectral data compression (in the case of PCR, this step is known as PCA), and linear regression. Using a linear combination of factors or principal components, a reconstructed spectrum is derived. This reconstructed spectrum is compared with the spectra of unknown specimens which serves as the basis for classification.

Prior to the analysis of unknown samples, another set of spectra of the same materials are typically used to validate and optimize the calibration. This second set of spectra enhance the prediction accuracy of the PCR or PLS model by determining the rank of the model. The optimal rank is determined from a range of ranks by comparing the PCR or PLS predictions with known diagnoses. Increasing or decreasing the rank from what was determined optimal can adversely affect the PLS or PCR predictions. For example, as the rank is gradually decreased from optimal to suboptimal, PCR or PLS would account for less and less variations in the calibration spectra. In contrast, a gradual increase in the rank beyond what was determined optimal would cause the PCR or PLS methodologies to model random variation rather than significant information in the calibration spectra.

Generally, the more spectra a reference set includes, the better is the model, and the better are the chances to account for batch to batch variations, baseline shifts and the nonlinearities that can arise due to instrument drifts and changes in the refractive index. Errors due to poor sample handling and preparation, sample impurities, and operator mistakes can also be accounted for so long as the reference data render a true representation of the unknown samples.

Another major advantage to using PCR and PLS analysis is that these methods measure the spectral noise level of unknown samples relative to the calibration spectra. Biological samples are subject to numerous sources of perturbations. Some of these perturbations drastically affect the quality of spectra, and adversely influence the results of a "diagnosis". Consequently, it is imperative to distinguish between spectra that conform with the calibration spectra, and those that do not (e.g. the outlier samples). The F-ratio is a powerful tool in detecting conformity or a lack of fit of a spectrum (sample) to the calibration spectra. In general F-ratios considerably greater than those of the calibration indicate "lack of fit" and should be excluded from the analysis. The ability to exclude outlier samples adds to the robustness and reliability of PCR and PLS as it avoids the creation of a "diagnosis" from inferior and corrupted spectra. F-ratios can be calculated by the methods described in Haaland, et al., *Anal. Chem.* 60:1193–1202 (1988), and Cahn, et al., *Applied Spectroscopy* 42:865–872 (1988).

When discriminating between samples of different cervical scrapings, the biological materials no longer have known concentrations of constituents, and/or a constant path length. As a result, the calibration spectra must determine the range of variation allowed for a sample to be classified as a member of that calibration, and should also include preprocessing algorithms to account for diversities in path length. One normalization approach that aids in the discrimination of cervical specimens is locating the maximum and minimum points in a spectral region, and rescaling the spectrum so that the minimum remains at 0.0, and the maximum at 1.0 absorbance (e.g. in the frequency region between 3000 cm$^{-1}$ to 1000 cm$^{-1}$). Another normalization procedure is to select a specific peak(s) at a certain frequency(ies) of the IR spectra, and relate all other peaks to the selected peak(s). A third type of normalization is to normalize the magnitude of the absorbance vector before processing.

In preferred embodiments, comparison of the infrared absorption data for the sample and the data for the calibration/reference set utilizes principal component analysis in the frequency region 1200 cm$^{-1}$ to 1000 cm$^{-1}$, more preferably in the frequency regions of about 1250 cm$^{-1}$ to 1000 cm$^{-1}$, about 1420cm$^{-1}$ to 1330 cm$^{-1}$ and about 3000 cm$^{-1}$ to 2800 cm$^{-1}$.

The Pap screening process renders a diagnosis based on the microscopic examination of each of the cells in a cervical scraping. Nevertheless, present spectroscopic techniques have used a bulk analysis of cervical scrapings. The use of Fourier Transform IR (FT-IR) spectroscopy, while capable of examining objects with sizes approaching 10 μm, is complicated by the presence of blood, mucus, and nondiagnostic debris in cervical scrapings. These materials can contribute to the clumping of the cells, and also create interferences that mask the actual spectra of cells in general. Nevertheless, it remains important to conclusively identify those cells that contribute to the changes in the spectra between normal and abnormal specimens. Thus, in one group of embodiments, the present method is carried out using a beam of mid-infrared light which is directed through an aperture of individual cell size, thereby providing absorption data for single cells. In this group of embodiments, the sample is dispersed and filtered, as described above, to create a uniform suspension of cells which can be applied to an infrared matrix and dried.

In a further aspect, the present invention provides a method for the in vivo identification of a malignant or premalignant cervical condition in a host, comprising:

(a) directing a beam of infrared light through an optic fiber at the cervical cells in the host, at a range of frequencies to produce absorption data for the cervical cells of the host; and (b) comparing the absorption data for the cervical cells with a calibration/reference set of infrared absorption data to determine whether variation in infrared absorption occurs in the cervical cells, at at least one range of frequencies, due to the variation being characteristic of a malignant or premalignant condition, the comparing utilizing a partial least squares or principal component analysis statistical method and the absorption data being underivatized and unsmoothed, whereby an identification of a malignant or premalignant condition is made.

In preferred embodiments, the calibration/reference set of infrared absorption data from cervical cells is obtained from a representative group of females with varying degrees of cervical conditions including, but not limited to dysplasia and cancer.

In the mid infrared region, use of the frequencies between 3000 $cm^{-1}$ to 950 $cm^{-1}$ is preferred. In the near IR, use of the frequencies between 12,500 $cm^{-1}$ to 4000 $cm^{-1}$ is preferred.

The techniques used in this aspect of the invention are generally the same as those described above. Differences are in the fundamental approach of in vivo collection of data and in the use of an optic fiber to direct the beam of mid or near infrared light. Typical optic fibers used for mid-Infrared include Chalcogenide, and Silver Halide. A typical optic fiber for near IR is the Quartz fiber. One advantage to in vivo analysis of cervical cells is that the method directs the physician to the site of abnormal tissue, and also minimizes the size of specimens for biopsy. Moreover, this method can provide a rapid objective screening of patients, while patients are being examined in a doctor's office. The current procedures necessitate that a physician sends Pap smears to a laboratory, where they are stained and evaluated by a cytotechnologist. Other benefits to the in vivo technique include the on-site treatment of suspicious tissues after localization by infrared spectroscopy.

In another aspect, the invention is a method for identifying a patient at high risk for dysplasia.

The method involves;

(a) creating a reference set of absorption spectra from cervical cells taken from women having no history of dysplasia, each of said samples having a combination of cells exhibiting at least one first spectrum pattern and at least one second spectrum pattern differing from each other in either source or pattern;

(b) producing absorption data for a cervical cell sample;

(c) comparing the absorption data with the reference spectra, whereby an identification of the high risk for dysplasia is made.

The techniques of sample preparation enumerated above can be used in conjunction with this aspect of the invention. Additionally, the sample under study can be a dried cell sample, or a sample which has not been dried. In certain preferred embodiments, the spectroscopic technique used to generate the sample and reference spectra is selected from the group consisting of infrared spectroscopy, nuclear magnetic resonance spectroscopy, ultraviolet spectroscopy and flow cytometry. In other preferred embodiments, the phenotype of the cells in the reference set is determined by Pap cytology. In still other preferred embodiments, the method uses infrared spectroscopy to generate the first and second spectrum patterns.

Figure 8:
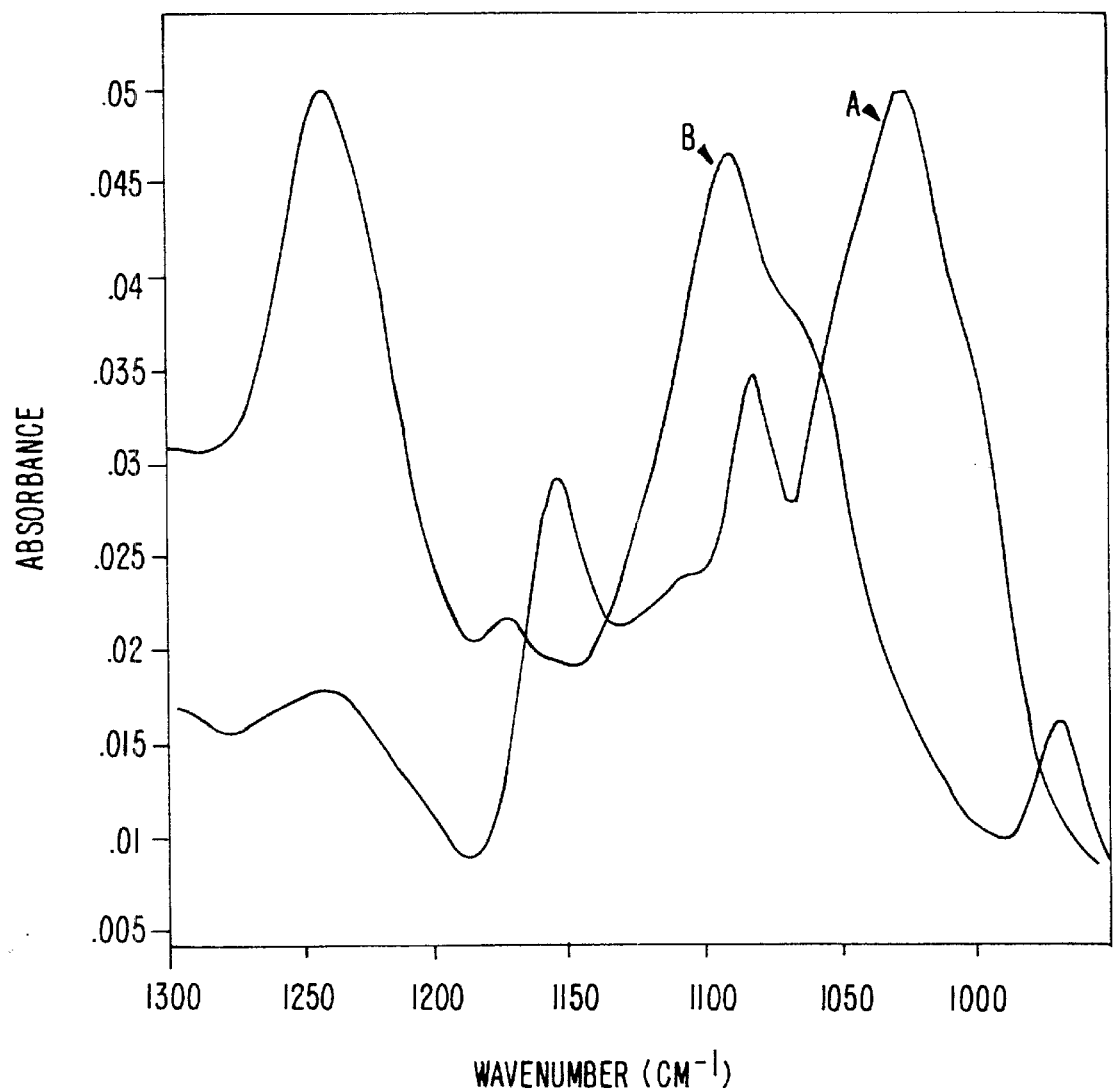
FIG. 8 shows two typical mid-infrared spectra (from 1000 $cm^{-1}$–1300 $cm^{-1}$) of individual normal cells in a cervical smear.

In the embodiment of the invention utilizing infrared spectroscopy, the reference set of absorption spectra is selected from infrared spectra with patterns corresponding to those defined as Pattern I and Pattern II (FIGS. 8A and 8B, respectively) and linear combinations of Pattern I and Pattern II. Pattern I is distinguished by an absorption maximum at about 1025 $cm^{-1}$ and additional discrete bands peaking at about 1080 $cm^{-1}$, 1160 $cm^{-1}$ and a broad peak at about 1250 $cm^{-1}$. Pattern II spectra are characterized by a significant reduction in the amplitude of the peak at 1025 $cm^{-1}$ and a broadening of the peaks at 1080 $cm^{-1}$ and 1250 $cm^{-1}$. Linear combinations of Pattern I and Pattern II spectra appear as hybrids of these two spectral patterns.

In embodiments of this aspect using mid-infrared light, use of the frequencies between 3000 $cm^{-1}$ to 950 $cm^{-1}$ is preferred. In the near IR, use of the frequencies between 12,500 $cm^{-1}$ to 4000 $cm^{-1}$ is preferred.

In an additional aspect, the invention provides FT-IR microspectroscopic methods for detecting chemical differences between a cell sample and a reference cell sample.

The method comprises:

(a) directing a beam of infrared light at individual cells in a cell sample to produce absorption data for the individual cells;

(b) comparing the absorption data from the individual cells with infrared absorption spectra acquired from at least one reference cell sample to generate comparison data;

(c) generating predicted scores for the comparison data of individual cells by utilizing multivariate analysis of the comparison data; and (d) creating frequency distribution profiles from the predicted scores, whereby the infrared microspectroscopic detection of chemical differences is achieved.

In preferred embodiments of the above aspects of this invention, the beam of infrared light has a frequency of from about 3000 $cm^{-1}$ to about 950 $cm^{-1}$, or from about 12,500 $cm^{-1}$ to about 3000 $cm^{-1}$. In other preferred embodiments, the chemical difference is associated with a malignant or premalignant phenotype. In further preferred embodiments, the cell sample contains cells taken from the bladder, breast, male or female reproductive system (e.g. prostate, testicles, ovaries, uterus, etc.), central nervous system, blood, liver, bone, colon, pancreas or other organs or structures. In certain most preferred embodiments, the cell sample contains cervical cells and the method of the invention is utilized to distinguish between cells exhibiting normal, normal-dysplastic, dysplastic and malignant phenotypes. In additional preferred embodiments the data acquired from the cell sample and the spectra acquired from the reference sample are compared at one or more frequency ranges selected from the group consisting of 1200 $cm^{-1}$ to 1000 $cm^{-1}$, more preferably in the frequency regions of about 1250 $cm^{-1}$ to 1000 $cm^{-1}$, about 1420 $cm^{-1}$ to 1330 $cm^{-1}$ and about 3000 $cm^{-1}$ to 2800 $cm^{-1}$. In still further preferred embodiments the multivariate analysis of the data can use one or more techniques selected from the group consisting of PLS, PCR and PCA.

In the discussion which follows, cervical cell samples are utilized as a representative example. Further, for purposes of clarity, only normal, malignant and varyingly dysplastic cells are discussed. It will be apparent to one of skill in the art that the methods of the invention are broadly applicable to a range of cell types and diseases.

The techniques of sample collection and preparation used in this aspect of the invention can be generally the same as those described above. Further, the methods of data processing useful in conjunction with this aspect of the invention are generally similar to those outlined above. Additionally, the infrared absorption data constituting the reference set can be similar to that discussed above with respect to the method for identifying a patient at high risk for developing dysplasia.

It will appreciated by those of skill in the art that additional aspects of this invention, wherein the sample is either dried or not dried are within the scope of the instant invention. Additionally, in those embodiments of the invention utilizing light in the near infrared region, sample holders made of a material appropriate for use in this region such as those made of glass, quartz or $CaF_2$ are contemplated by the invention.

Infrared microspectroscopy is a useful technique for single cell chemical analysis (see Yang, D., et al., *J. Clin. Laser Med. Surg.*, 13:55–59 (1995)). A fundamental difference between bulk FT-IR spectroscopy, and FT-IR microspectroscopy lies in the spatial selectivity of the procedures. In bulk spectroscopy, the IR beam is directed towards all components of a cervical scraping, cellular and non-cellular, and no specific components or cells in the Pap smear can be targeted for spectral acquisition. Consequently, in bulk spectroscopy, the final spectrum represents the average spectra of all components in a cervical scraping. In microspectroscopy, on the other hand, the IR beam can be directed towards any of several objects within a smear. For example, if the spectra of only red blood cells are desired, the microscope stage is simply moved so as to position the red blood cells in the path of the IR beam. In addition to its ability to select objects, FT-IR microspectroscopy is also a sensitive method allowing the study of objects with sizes approaching the diffraction limit. Consequently, this method can provide a spectrum of each type of cervical cell; whether be it a 7–12 micron parabasal, or endocervical cell, or a 35–45 micron intermediate squamous epithelial cell.

Utilizing IR microspectroscopy, it can be demonstrated that it is the infrared spectra of individual cells which allow the chemical changes in a cell sample to be detected. For example, it is the infrared spectra of individual cervical cells in a cervical cell scraping that allow for the discrimination between normal, dysplastic and malignant cervical scrapings. More importantly, techniques have been developed and are described herein (see Examples 5–8), for constructing distribution profiles of spectra of individual cells based on predicted scores generated by Principle Component Analysis (PCA) and Partial Least Squares (PLS). Alternatively, constructing the distribution profiles can rely on one or more techniques selected from the group consisting of PLS, PCR and PCA. The distribution profiles can be used to diagnose normal and diseased cells in a cell sample. For example, distribution profiles generated from cervical cell samples display a clear-cut separation between the spectra of cells in "normal" smears (i.e., smears that were cytologically diagnosed as normal and which were derived from women with no prior history of dysplasia) and in smears with "normal-dysplasia" (i.e., smears that were cytologically diagnosed as normal and which were derived from women with a past history of dysplasia). The distribution profiles allow the cells to be classed according the presence or absence of distinctive chemical changes associated with disease states.

In a related aspect, the invention is an infrared microspectroscopic method for discriminating between normal, premalignant and malignant cells in a cell sample. The techniques and preferred embodiments of this aspect of the invention are generally the same as those described above for detecting chemical differences between a cell sample and a reference set. An important feature of this aspect of the invention is that the cells of the reference set are cytologically determined to correspond to a normal, malignant or premalignant phenotype. In one preferred embodiment, the calibration/reference set comprises a first IR spectrum and a second IR spectrum differing from each other by either source or spectral pattern and each corresponding to a spectral pattern independently selected from the group consisting of Pattern I and Pattern II, and the first IR spectrum and the second IR spectrum are derived from cells independently selected from the group consisting of normal, normal-dysplastic, dysplastic and malignant cells.

In an additional aspect, the invention provides an infrared imaging method for detecting chemical differences between a cell sample and a reference cell sample.

The method comprises:
(a) directing a beam of infrared light at a cell sample to produce absorption data for the cell sample;
(b) comparing the absorption data from the cell sample with a calibration/reference set of absorption spectra constructed by pixel-by-pixel analysis of infrared absorption spectra acquired from at least one reference cell sample to generate comparison data;
(c) generating predicted scores for said comparison data utilizing multivariate analysis of the comparison data; and
(d) creating frequency distribution profiles from the predicted scores, whereby the infrared imaging detection of chemical differences is achieved.

In one embodiment of this aspect of the invention, the cell samples are cervical cell samples, preferably exfoliated, containing normal, normal-dysplastic, dysplastic and malignant cells. In still other preferred embodiments, the beam of infrared light is in the mid infrared region and has a frequency of from about 3000 $cm^{-1}$ to about 950 $cm^{-1}$. In further preferred embodiments, the beam of infrared light is in the near infrared region and has a frequency of from about 4000 $cm^{-1}$ to about 12000 $cm^{-1}$. In particularly preferred embodiments, the calibration/reference set of infrared absorption data is obtained from a representative set of cytologically determined normal, dysplastic and malignant cervical cells which were dried on an infrared transparent matrix.

The techniques of sample preparation used in this aspect of the invention are generally the same as those described above in connection with infrared microspectroscopy. The methods for processing the data are also generally similar to those outlined above with the notable exception that the data is analyzed on a pixel-by-pixel basis.

In a related aspect of the invention, infrared imaging is used to distinguish between cell samples which are normal, premalignant and malignant. In this aspect of the invention, the phenotype of the reference cells is determined cytologically. The techniques used in this aspect are substantially similar to those described with respect to infrared imaging to detect chemical differences between cells. A preferred embodiment of this aspect of the invention is directed to the study of exfoliated cervical cells.

Recent technological advances in infrared spectrometer detector technology have made possible the development of infrared spectroscopic imaging. The application of infrared spectroscopic imaging to the analysis of cells in a cervical cell sample is discussed herein.

Vibrational spectroscopic imaging is a comparatively new imaging modality with utility in the biological, chemical and material sciences (Lewis, E. N., et al. *Anal. Chem.,* 67:3377–3381 (1995)). A flexible and robust technique, vibrational spectroscopic imaging combines the molecular identification powers of spectroscopic molecular analysis with the ability to visualize the morphology and regional chemical properties of a tissue sample through 2-D and, potentially, 3-D imaging. Further, vibrational spectroscopic imaging provides access to both qualitative and, through the application of Beer's Law, quantitative data about the distribution of the molecules of interest in the sample under investigation.

A typical near-IR imaging instrument utilizes a step-scan Fourier transform Michelson interferometer (Bio-Rad FTS-60A) coupled to an IR microscope (Bio-Rad UMA 500A) and an indium antimonide (InSb) focal plane array (FPA) detector (ImagIR, Santa Barbara Focalplane). The microscope optics and the interferometer electronics are modified to couple efficiently to the InSb detector. The optical modification consists of placing a $CaF_2$ lens between the microscope objective and the FPA. The electronic modification consists of adding a counter/timer board which synchronizes the stepping of the interferometer and the FPA detector. Data acquisition and processing is similar to that performed during a conventional FT-IR study. Briefly, the interferograms are organized as spectral image files (SPIFF) and Fourier transformed. The SPIFF files can be visualized using commercially available image processing and visualization software (e.g., ChemImage 1.0, ChemIcon, Optimas 4.02, etc.). A typical mid-IR imaging system will have many of the same components described above, but will differ in that the FPA can be a MCT (mercury cadmium telluride) detector. Also, the lens between the microscope objective and the detector can be $CaF_2$, glass or quartz.

Infrared microscopic imaging instruments are commercially available, e.g., Bio-Rad's FTS Stingray 6000 (Bio-Rad, Cambridge, Mass.). Infrared imaging is made possible by combining the multiplexing power of interferometry with a multichannel detector. The multichannel detector allows spectra at every pixel to be collected simultaneously and the interferometer allows all relevant wavelengths to be monitored concurrently. Currently, state-of-the-art FPA detectors have as many as one million detector elements and readout rates in excess of 16,000,000 pixels per second. The resolution of the images produced in IR imaging is limited only by the number of detector elements on the FPA. In addition, the FPA detectors can be constructed of materials that are sensitive to light in the wavelength range between 10,000 $cm^{-1}$–500 $cm^{-1}$. Finally, although a great quantity of data is collected in the typical IR imaging experiment (a 128×128 detector array gives 16,384 pixels) the multiplex/multichannel instrument set up affords rapid data acquisition. For example, Lewis and coworkers have reported collecting data sets containing 16,384 pixels at 16 $cm^{-1}$ resolution in only 12 seconds (Lewis, E. N., et al. *Anal. Chem.,* 67:3377–3381 (1995)).

One of skill in the art will understand, unless expressly stated otherwise, that general methods (e.g., for comparison of data, generation of predicted scores and generation of cut-off intervals) can be applicable to each of the recited aspects and embodiments of this invention.

EXAMPLES

The detailed examples which follow describe the methods of the invention as applied to distinguishing between normal, normal dysplastic, dysplastic and malignant cervical cells which are recovered during a routine cervical smear. The examples describe the use of bulk FT-IR spectroscopy, FT-IR microspectroscopy and FT-IR spectroscopic imaging.

Although much of the detailed discussion embodied herein relies on the use of cervical cells as a representative example, the use of this cell type is not intended to infer that the methods of the invention have utility with only cervical cell samples. It will be apparent to one of skill in the art that the methods can be extended with slight modification to the analysis of chemical between cells and/or diagnosis of disease states, in an array of different cell types. For example, the analysis of chemical changes and/or the diagnosis of disease states in cells of the breast, bladder, male or female reproductive system (e.g., prostate, ovaries, etc.), liver, lymph nodes, bone, pancreas and other organs or structures are within the scope of this invention. The above list is intended to be illustrative and not exhaustive. Thus, the following examples are offered solely for the purposes of illustration, and are intended neither to limit nor to define the invention.

Example 1 illustrates the detection of malignant and premalignant cervical cancer conditions using infrared spectroscopy in conjunction with principal component analysis (PCA). Example 2 provides a comparison of diagnosis of cervical abnormalities using a mid-infrared technique using partial least squares analysis (PLS), and Pap smears which are stained and examined by conventional microscopy. In Example 3, it is shown that there are close similarities between the spectra of cervical scrapings with dysplasia (as diagnosed by Pap cytology), and cervical scrapings which are diagnosed as normal (by Pap cytology), but which have a prior history of dysplasia (e.g. specimens with diagnosis "normal-dysplasia"). Example 4 illustrates the use of single cell FT-IR spectroscopy for the detection of malignant and premalignant conditions in cervical cells.

Examples 5–8 demonstrate the use of FT-IR microspectroscopy and the acquisition of spectra from single cells in a dried cervical cell sample to obtain data, subsequently processed by PCA and/or PLS. The processed data is used to construct distribution profiles for the spectra of phenotypically differentiated cells. The distribution profiles have a clearly demonstrable diagnostic utility and allow distinction between normal, normal-dysplastic, dysplastic and malignant cells.

Example 5 shows the construction of a calibration/reference set of IR spectra derived from diagnostically normal cells which exhibit distinct spectral patterns (Pattern I, Pattern II). Similarly, Example 6 demonstrates the construction of a calibration/reference set of IR spectra derived from normal cells exhibiting Pattern I spectra and dysplastic cells exhibiting Pattern II spectra. Example 7 illustrates a calibration/reference set composed of spectra from normal cells exhibiting Pattern I spectra and malignant cells with Pattern II spectra. Finally, Example 8 illustrates a calibration/reference set of IR spectra derived from normal cells with Pattern II spectra and malignant cells exhibiting Pattern II spectra. In examples 5–8, inclusive, the calibration/reference set was compared to FT-IR spectra from cervical smears. The comparison was made using PLS and/or PCR.

EXAMPLE 1

This example illustrates the detection of malignant and premalignant cervical cancer conditions using infrared spectroscopy with principal component analysis.

1.1 Materials and Methods

Four hundred thirty-six spectra were obtained from cervical scrapings collected by the method described in Wong, et al., *Proc. Natl. Acad. Sci. USA,* 88:10988–10992 (1991).

The spectra and Pap smear diagnosis were analyzed for the feasibility of predicting Pap smear diagnosis by principle component analysis of the infrared spectra. Unless otherwise indicated, analysis was confined to the frequency region of 1200 cm$^{-1}$ to 1000 cm$^{-1}$. All spectra were normalized in the frequency region of 1200 cm$^{-1}$ to 1000 cm$^{-1}$ so that the minimum absorbance was set at 0.0 absorbance and the maximum at 1.0 absorbance.

1.2 Results

Inspection of the spectra after normalization revealed two basic patterns. One pattern exhibited a prominent peak around 1025 cm$^{-1}$ (see FIG. 1), and had spectral features typical of those observed with normal cervical scrapings (see Wong, et al., ibid.). The second basic pattern manifested no peaks at or around the 1025 cm$^{-1}$ region (FIG. 2), and appeared 'typical' of the spectra which were reported for malignant specimens (Wong, et al., ibid.). In some cases, spectra appeared to be a mixture of the two patterns, and/or appeared atypical, or showed fringing. The initial analysis focused on samples that exhibited the 'typical' normal and malignant spectra, and excluded all other specimens with anomalous spectral features (e.g. with a mixed, or an atypical or fringed pattern).

TABLE 1

PCA ANALYSIS OF CALIBRATION DATA SET

| Rank | SS | Cumulative SS |
| --- | --- | --- |
| 1 | 70.03% | 70.03% |
| 2 | 15.07% | 85.11% |
| 3 | 7.76% | 92.86% |
| 4 | 3.77% | 96.63% |
| 5 | 1.50% | 98.13% |
| 6 | 0.72% | 98.85% |
| 7 | 0.40% | 99.25% |
| 8 | 0.24% | 99.49% |
| 9 | 0.18% | 99.68% |
| 10 | 0.12% | 99.80% |

Figure 2:
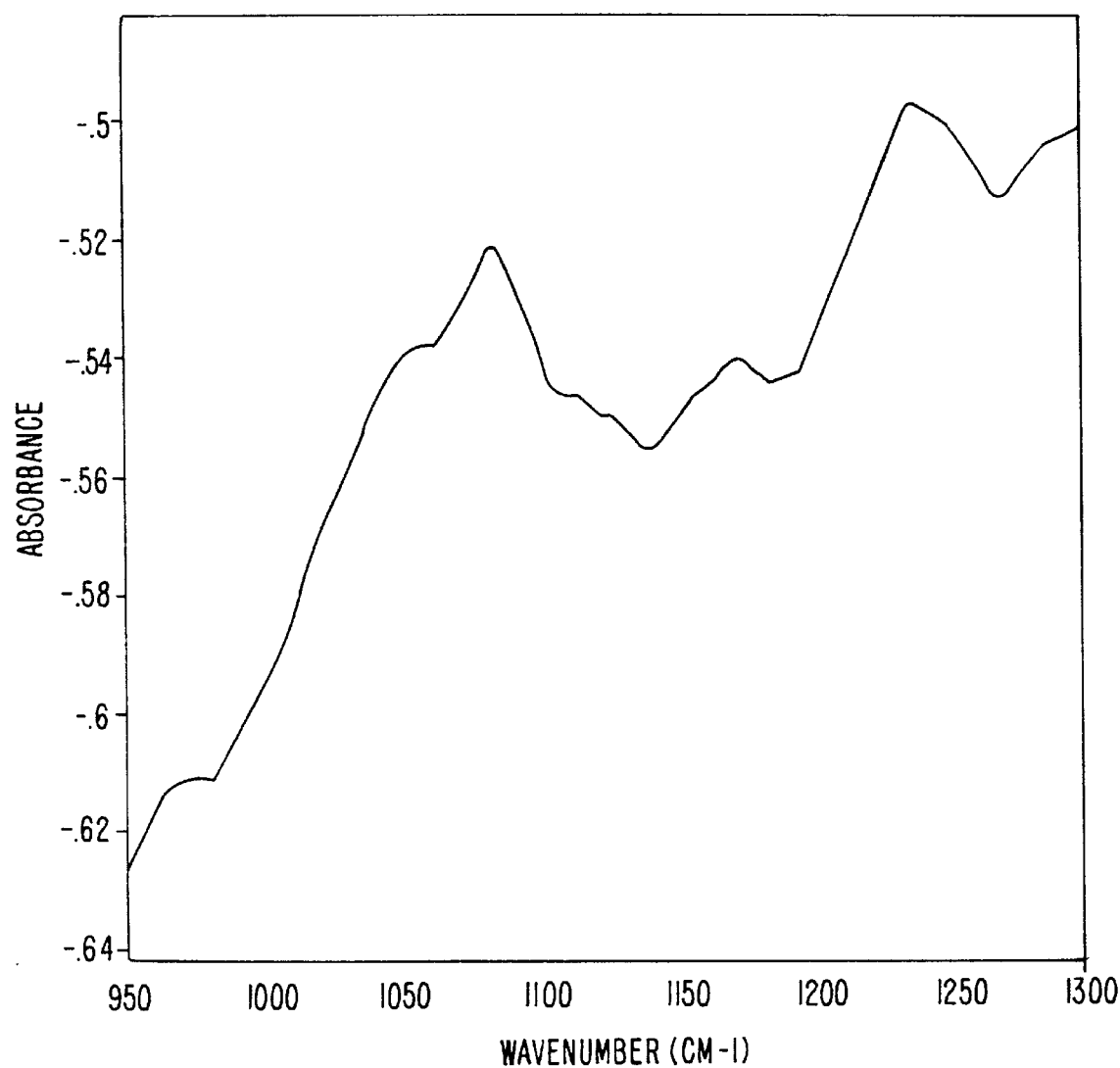
FIG. 2 shows the mid-infrared spectrum (from 950 $cm^{-1}$–1300 $cm^{-1}$) of a malignant cervical scraping.

A calibration set was then created on a subset of these preselected spectra as follows: one reference included the normal specimens with spectra 'typical' of normal cervical scrapings (FIG. 1), and the other of malignant samples with spectra typical of cancer (FIG. 2). Spectra from normal cervical scrapings were assigned a dummy variable value of 0, and those from malignant scrapings were assigned a value of 1. Every 4th spectrum was removed from the calibration set and was used as a validation sample.

Table 1 summarizes the Sum of Squares (SS) of the spectra after mean centering as elucidated by each principal component. Calculation of these values was carried out by the methods described in Haaland, et al., Anal. Chem. 60:1193–1202 (1988), and in Cahn, et al., Applied Spectroscopy 42:865–872 (1988). Tabulated results show that over 99% of the variation in the spectra are accountable by the first 7 principal components.

A rank of 7 was selected as providing the best discrimination on a cross validation analysis of the few randomly selected validation samples that were omitted from the calibration. This rank was selected on the basis of tabulating the minimum prediction of the malignant samples and the maximum prediction for the normal samples vs. PCR model rank (Table 2).

TABLE 2

PREDICTED DUMMY VARIABLES vs. PCR MODEL RANK

| Rank | Minimum malignant prediction | Maximum normal prediction |
| --- | --- | --- |
| 1 | 0.93 | 0.14 |
| 2 | 0.95 | 0.10 |
| 3 | 0.92 | 0.16 |
| 4 | 0.92 | 0.19 |
| 5 | 0.90 | 0.09 |
| 6 | 0.94 | 0.09 |
| 7 | 0.95 | 0.08 |
| 8 | 0.95 | 0.08 |
| 9 | 0.95 | 0.12 |
| 10 | 0.94 | 0.11 |

Figure 3:
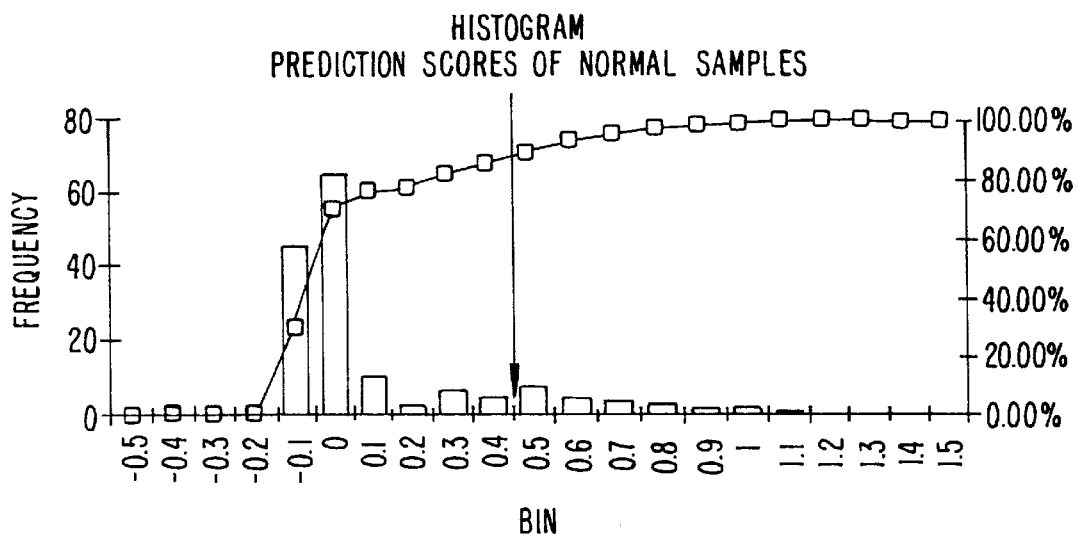
FIG. 3 is a histogram showing the prediction of scores of normal samples in bulk.
Figure 4:
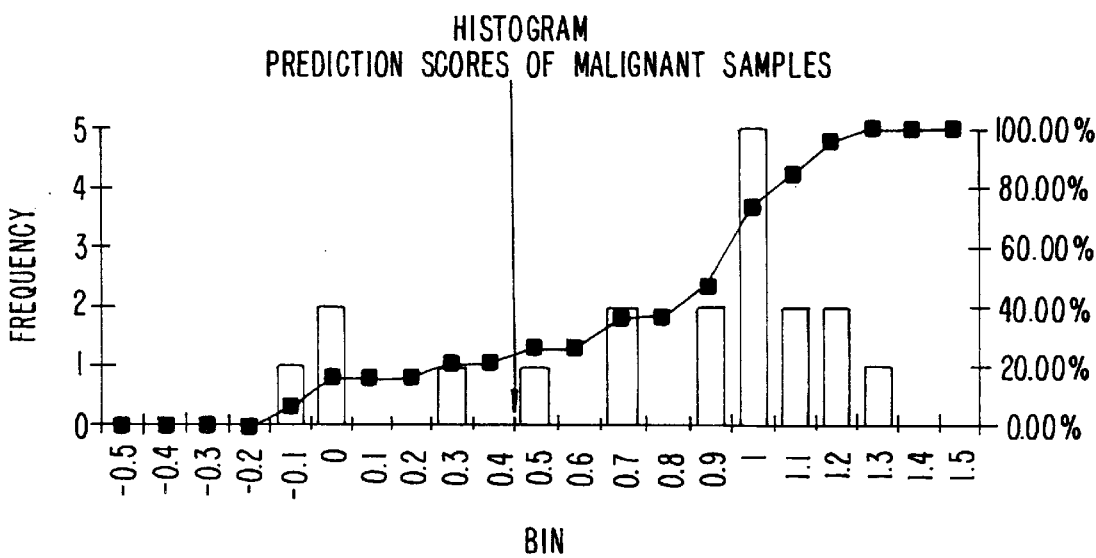
FIG. 4 is a histogram showing the prediction of scores of malignant samples in bulk.

At rank 7, the minimum prediction of the dummy variable among malignant validation samples was 0.95 (closest to 1.0), and the highest prediction of the dummy variable among normal validation samples was 0.08. Rank 7 was thereafter used to analyze the entire set of the 436 spectra. Histograms were then computed for the predicted dummy variable using 162 normal and 19 malignant samples. A break point (BP) of 0.5 provided a reasonable discrimination between the normal and malignant spectra (see FIGS. 3 and 4).

1.3 PCA Analysis of All Spectra

F-ratios were calculated for all spectra from the sample set. These values were calculated according to the methods described in Haaland, et al., Anal. Chem. 60:1193–1202 (1988). The F-ratios provide an indication of how similar a sample spectrum is to the calibration set. High F ratios, for examples, can result when a sample is dissimilar to the calibration spectra being analyzed. In this study, all spectra with F ratios $\geq 25$ were by visual inspection found to be either corrupt or significantly distinct from the calibration spectra.

A F-ratio $\geq 25$ was, thus, arbitrarily selected as the rejection threshold for exclusion of outlier spectra. This selection provides a consistency (which cannot be obtained by purely visual inspection) to the set of spectra which are then used for diagnosis. Based on this criterion, 40/436 samples were flagged out as specimens with a "poor" spectrum. Table 3 summarizes the diagnosis code, and the number of specimens that remained in each diagnosis class after exclusion by the F ratio criterion.

Based on a 0.5 breakpoint, the 396 samples having F-ratios below 25 were classified as normal or malignant according to this linear discriminate function on the spectra. The following contingency table (Table 4) summarizes the results.

Table 4 was based on the null hypothesis that with the exclusion of the malignant specimens (e.g., code m), there was no difference in the predicted distribution of each individual diagnosed category. A Chi Square test of the null hypothesis yielded a value of 44.9 at 21 degrees of freedom. The null hypothesis is rejected at the p=0.002 significance level, suggesting that at least some of the diagnoses are associated with a different frequency than being predicted as normal by spectroscopy. The computation of the Chi Square value ($\chi^2$) was performed by standard statistical methods, by excluding the malignant samples (code m) as follows: First, the sum of the numbers in column O and column m were calculated. These numbers were found to be 286 and 91, respectively. Next, for each of the "observed" values, an expected value was calculated. These expected values in column O were calculated on the basis of multiplying (the total sum of each row) by (the total sum of the observed numbers in column O divided by 377). The number 377 represents the total of all rows. For example, the "expected" value of 39.4 in column O for diagnosis atypical (code a) resulted from taking the number 52 (e.g., the total sum of the row)×(286÷377).

TABLE 3

| Diagnosis Code | Total Specimens | Pap smear report |
|---|---|---|
| 0 | 174 | Normal |
| a | 52 | Atypical |
| ab | 4 | Atypical with a bloody smear |
| abi | 4 | Bloody smear with atypical cells and inflammatory signs |
| ai | 27 | Atypical with evidence of inflammation |
| air | 5 | Atypical (reactive) with evidence of inflammation |
| ar | 19 | Atypical (reactive) |
| at | 2 | Atypical with atrophic pattern |
| b | 6 | Bloody smear |
| bi | 2 | Bloody smear with evidence of inflammation |
| br | 2 | Bloody smear with reactive cells |
| bx | 2 | Bloody and an acelfular smear |
| d | 8 | Dysplasia |
| i | 30 | Inflammatory |
| ib | 1 | Inflammatory and bloody smear |
| ir | 7 | Inflammatory with reactive cells |
| it | 4 | Inflammatory with atrophic pattern |
| m | 19 | Malignant or carcinoma in situ |
| r | 4 | Reactive |
| rt | 1 | Reactive with atrophic pattern |
| t | 19 | Atrophic pattern |
| tx | 3 | Acellular with atrophic pattern |
| x | 1 | Acellular |
| Total | 396 | |

TABLE 4

CONTINGENCY TABLE BASED ON 0.5 BREAKPOINT

| | | Observed | | Expected | | | |
|---|---|---|---|---|---|---|---|
| Diagnosis | Total | 0 | m | 0 | m | $\chi^2$ | p |
| 0 | 174 | 148 | 26 | 132 | 42 | | |
| a | 52 | 39 | 13 | 39.4 | 12.6 | 2.18 | 0.140 |
| ab | 4 | 1 | 3 | 3.03 | 0.97 | 6.41 | 0.011 |
| abi | 4 | 2 | 2 | 3.03 | 0.97 | 1.46 | 0.226 |
| ai | 27 | 21 | 6 | 20.5 | 6.52 | 0.46 | 0.497 |
| air | 5 | 3 | 2 | 3.79 | 1.21 | 0.80 | 0.370 |
| ar | 19 | 16 | 3 | 14.4 | 4.59 | 0.06 | 0.810 |
| at | 2 | 0 | 2 | 1.52 | 0.48 | 5.28 | 0.022[I] |
| b | 6 | 3 | 3 | 4.55 | 1.45 | 3.00 | 0.083 |
| bi | 2 | 1 | 1 | 1.52 | 0.48 | 0.15 | 0.703 |
| br | 2 | 2 | 0 | 1.52 | 0.48 | 0.17 | 0.682 |
| bx | 2 | 1 | 1 | 1.52 | 0.48 | 0.15 | 0.703 |
| d | 8 | 4 | 4 | 6.07 | 1.93 | 4.52 | 0.034 |
| i | 30 | 21 | 9 | 22.8 | 7.24 | 3.09 | 0.079 |
| ib | 1 | 1 | 0 | 0.76 | 0.24 | 0.98 | 0.322[I] |
| ir | 7 | 6 | 1 | 5.31 | 1.69 | 0.24 | 0.622 |
| it | 4 | 3 | 1 | 3.03 | 0.97 | 0.02 | 0.880 |
| m | 19 | 4 | 15 | — | — | 38.2. | 0.000* |
| r | 4 | 2 | 2 | 3.03 | 0.97 | 1.46 | 0.226 |
| rt | 1 | 0 | 1 | 0.76 | 0.24 | 0.92 | 0.337[I] |
| t | 19 | 9 | 10 | 14.4 | 4.59 | 13.65 | 0.000* |
| tx | 3 | 2 | 1 | 2.28 | 0.72 | 0.00 | 0.945 |
| x | 1 | 1 | 0 | 0.76 | 0.24 | 0.98 | 0.322[I] |
| Totals: | 396 | 290 | 106 | | | | |
| Totals | 377 | 286 | 91 | | | | |

*denotes that a rounding of the number resulted in a p = 0.000.
 denotes that totals were subtracted from the samples with diagnosis malignant (code m)
[I]denotes that the method used to calculate the $\chi^2$ values necessitates the exercise of caution when interpreting the p values having a zero in one of the "observed" cells.

The "expected" values in column m were calculated by the same method except for multiplying (the total sum of each row) by (the total sum of the observed numbers in column m÷377). Once again, using the atypical diagnosed samples (code a) as an example, the "expected" value of 12.6 in column m was calculated by taking the number 52 (e.g., the total sum of the row)×(91÷377). Table 5 uses the first 4 rows of the contingency table to illustrate the overall mathematical manipulations that were employed in arriving at the $\chi^2$ value.

TABLE 5

| | Observed (O) | | Expected (E) | | $(O-E)^2$ | | $(O-E)^2/E$ | |
|---|---|---|---|---|---|---|---|---|
| Diagnosis | 0 | m | 0 | m | 0 | m | 0 | m |
| 0 | 148 | 26 | 132 | 42 | $(148-132)^2$ | $(26-42)^2$ | 1.94 | 6.09 |
| a | 39 | 13 | 39.4 | 12.6 | $(39-39.4)^2$ | $(13-12.6)^2$ | .004 | .013 |
| ab | 1 | 3 | 3.03 | 0.97 | $(1-3.03)^2$ | $(3-0.97)^2$ | 1.36 | 4.25 |
| abi | 2 | 2 | 3.03 | 0.97 | $(2-3.03)^2$ | $(2-0.97)^2$ | 0.35 | 1.09 |

$\chi^2 = \Sigma(O-E)^2/E$
= Sum of the numbers in column A + Sum of the numbers in column B for all diagnoses (with the exclusion of the malignant samples)
= 44.9 (a $\chi^2$ value of 44.9 at 21 degrees of freedom yields p = 0.002 from a $\chi^2$ distribution table)

With such a significant probability (e.g. p=0.002) for the contingency table as a whole, attempts were then made to find out which diagnosis class had a predicted distribution different than the normal samples. Accordingly, Chi Square tests (with Yates correction) were, once again, computed but this time for individual 2×2 subtables, each taken with the first row (normal diagnosis). If a, b, c, and d were to represent the numbers in the cells of the 2×2 tables as shown.

| Diagnosis | Observed | |
|---|---|---|
| | a | b |
| | c | d |

$x^2$ was calculated as follows:

$$\frac{[\text{absolutevalueof}(ad - bc) - 0.5(a + b + c + d)]^2 [a + b + c + d]}{(a + b)(c + d)(b + d)(a + c)}$$

Thus, with the malignant samples, as an example:

| | Observed | |
|---|---|---|
| Diagnosis | O | m |
| O | 148 | 26 |
| m | 4 | 15 |

$$\chi^2 = \frac{[\text{absolutevalueof}(148 \times 15 - 26 \times 4) - (0.5(148 + 26 + 4 + 15)])^2 [148 + 26 + 4 + 15]}{(148 + 26)(4 + 15)(26 + 15)(148 + 4)}$$

$x^2 = 38.2$ (based on a $x^2$ distribution table, a $x^2$ value of 38.2 corresponds to a p < 0.001)

A diagnosis category with a high probability value (p) indicates that samples within that category have a distribution similar to the normal specimens. While those with low probability are distributed differently. Thus, as shown in Table 4, highly significant frequencies of being predicted "malignant" were associated with samples which were diagnosed malignant, as expected (p<0.001). Also highly significant was the prediction for samples diagnosed with "atrophic pattern" (p<0.001). In addition, prediction frequencies were significantly higher than expected (p≦0.05) for specimens diagnosed as atypical with bloody smear, atypical with atrophic pattern and dysplasia (e.g., diagnosis codes ab, at, and d, respectively).

There are other ways to analyze such a contingency table (Table 4) that can be advantageous for statistical accuracy. For example, the routine "PROC FREQ" in the SAS library of statistical routines (The SAS Institute Inc., Cary, N.C.) can be used to compute the probability of the null hypothesis of this entire table as well as the 2×2 contingency tables. This routine can also compute "Fisher's Exact" test, which might be preferred when some of the cells in the table are zero. Another approach that could be used to compute the probability that the distribution of the samples in one or more of the diagnosis subgroups differ from that of the sample with normal diagnosis would be to aggregate the data for all the different diagnoses (preferably excluding diagnosis of 0, d, and m, for which there is an expectation of such a difference) before constructing a 2×2 table of normal vs. all other diagnoses, which can be analyzed by the Chi Square test.

EXAMPLE 2

This example provides a comparison of diagnosis with a mid-infrared technique using partial least squares analysis, and Pap smears applying conventional microscopy.

2.1 Specimen Collection

Cervical scrapings were collected by the standard brushing procedure. Exfoliated cells from each brush were harvested in separate vials which contained normal saline. The cell suspensions in each vial were dispersed with a Pasteur pipette and divided into two equal portions. One portion of the cell suspension was centrifuged and the pellet was stored frozen in liquid nitrogen until spectroscopic analysis. The other portion was spread on a microscope slide, fixed and stained by Papanicolaou stain and was examined by at least one pathologist. Out of 302 cervical scrapings that were analyzed, 206 samples were obtained from a dysplasia clinic and 96 specimens were obtained from an outpatient gynecology clinic. Three types of diagnosis were assigned to the specimens. Specimens which showed no evidence of cytological abnormality and which were obtained from individuals who had no history of cervical anomaly were classified as "normal-normal". Specimens which had normal cytology, and which were obtained from individuals who had a prior history of dysplasia were labeled as "normal-dysplasia". Specimens which exhibited evidence of dysplasia were classified according to the extent of disease using standard nomenclature. Samples which were found to have the human papilloma virus were designated with the letters "HPV", and were included in the samples diagnosed as "dysplasia".

Table 6 summarizes the number and the diagnosis of each type of specimen.

2.2 Spectroscopic Analysis

The thawed pellets of cervical scrapings were analyzed spectroscopically, as follows: cervical scrapings were mixed with a Pasteur pipette in a syringing action, and the cell suspensions were then smeared and dried on Cleartran windows (ZnS). Mid-infrared spectra were obtained at room temperature on a Bio-Rad, Digilab FTS 165 spectrometer equipped with a DTGS detector. Spectra were collected at a resolution of 4 cm$^{-1}$ and 100 scans were co-added. A single-beam spectrum of Cleartran window was used for a background reference with each spectrum. Each spectrum was also normalized by setting the minimum absorbance at 0.0 and the maximum absorbance at 1.0. Drying of the samples resulted in specimens which were easy to manipulate and which yielded high quality spectra.

TABLE 6

| Specimen Type | Number |
| --- | --- |
| Normal-Normal | 96 |
| Normal-Dysplasia | 152 |
| Type of Dysplasia | |
| CIN I | 30 |
| CIN II | 5 |
| CIN III | 3 |
| CIN I-II | 8 |
| CIN II-III | 1 |
| CIN I-HPV | 4 |
| CIN II-HPV | 1 |
| HPV | 2 |
| Total no. of specimens | 302 |

2.3 Partial Least Squares Analysis

Out of the 302 spectra that were selected for PLS analysis, 54 spectra were from specimens that had the diagnosis of dysplasia, 152 spectra were from specimens with diagnosis 'normal-dysplasia', and 96 spectra were from samples with diagnosis 'normal-normal'. One subset of the dysplastic and the 'normal-normal' spectra was then used to create a calibration set. Unless otherwise indicated, the 'normal-normal' specimens that were included in the calibration (reference) set all had spectra that appeared similar or identical to the spectrum in FIG. 1 (e.g. the spectrum reported by Wong and co-workers to characterize normal cervical scrapings). The reference specimens with dysplasia were assigned a dummy variable value of 1, and the 'normal-normal' references were assigned a value of 0. Spectra that were not included in the calibration set were used as validation samples. A break point (BP) of 0.5 was used to discriminate between the samples. All specimens with a predictive break point value <0.5 were classified as normal, and those with a predictive value $\geq 0.5$ were classified as abnormal.

2.4 Results

Three spectral regions were utilized in the analysis of the data. These regions included the zones between 1250–1000 cm$^{-1}$, 1420–1330 cm$^{-1}$, and 3000–2800 cm$^{-1}$. Rank 8 was selected as providing the best discrimination between the samples. A F-ratio $\geq 17$ was arbitrarily selected as the rejection threshold for exclusion of outlier spectra. Table 7 summarizes the results of PLS with the validation samples (e.g. 27 dysplasia, 44 "normal-normal" and 152 "normal-dysplasia" specimens).

TABLE 7

| Diagnosis | Total Number | Total Samples with F ratios < 17 | Observed N | D | $\chi^2$ |
| --- | --- | --- | --- | --- | --- |
| Normal-Normal | 44 | 40 | 31 | 9 | |
| Normal-Dysplasia | 152 | 146 | 49 | 97 | 23 p < 0.001 |
| Dysplasia | 27 | 27 | 3 | 24 | 25.8 p < 0.001 |
| Total | 223 | 213 | | | |

N and D denote samples which were predicted as "Normal-Normal", and "Dysplasia", respectively.

As shown in Table 7, a total of 10 samples (e.g., 4 "normal-normal", and 6 "normal-dysplasia") were excluded from the study. Each of the excluded samples had a F ratio $\geq 17$. A Chi Square analysis of 2×2 subtables each taken with the first row ("normal-normal" diagnosis) based on the null hypothesis that there was no difference in the predicted distribution of specimens identified as "normal-normal", and specimens with "normal-dysplasia" or "dysplasia" yielded $\chi^2$ values of 23, and 25.83, respectively. The null hypothesis is rejected for both the "normal-dysplasia", and the "dysplasia" specimens at the p<0.001 significance level. As shown in Table 7, highly significant frequencies of predicting samples with dysplasia were associated with dysplasia samples. Also highly significant was the difference in the distribution of specimens classified as "normal-dysplasia" relative to the "normal-normal" samples.

These results demonstrate the potential of PLS in discriminating between "normal-normal" specimens, and specimens with existing or with a prior history of dysplasia.

Example 3

This example illustrates that there are close similarities between the spectra of cervical scrapings with dysplasia, and cervical scrapings which are diagnosed as normal, but which have a prior history of dysplasia (e.g. specimens with diagnosis "normal-dysplasia").

A calibration set consisting of spectra from samples with known dysplasia, and from samples with "normal-dysplasia" using the prior data was constructed. The purpose of this analysis was to determine whether the spectra of cervical scrapings with dysplasia appeared different than the spectra of cervical scrapings with 'normal-dysplasia'. Using PCA and discriminate analysis, no significant discrimination between the two populations was observed. In the absence of observable differences, this analysis suggests that regardless of the cytological appearance of the Pap smear, in a majority of patients who have had a prior history of dysplasia the method applied to the IR spectra detects abnormal findings. Hence, IR spectroscopy, as practiced here, provides additional diagnostic information, not available by the standard cytological examination of cervical smears. Bearing in mind that the genesis of a majority of cervical dysplasias is believed to be caused by the human papilloma virus, these abnormal spectral features can directly relate to the presence of the HPV virus in the cervical scrapings of patients classified with 'normal-dysplasia'.

The IR methods of this invention can thus discriminate between a population of women having no history of dysplasia or malignancy, and one of women who are either diagnosed with dysplasia or malignancy (as detected by Pap cytology) or who have a history of dysplasia in the absence of a current diagnosis for dysplasia by Pap cytology (e.g., patients who are clinically at a high risk for dysplasia).

Example 4

This example illustrates the use of single cell infrared spectroscopy for the detection of malignant and premalignant conditions in cells.

Recent infrared spectroscopic studies of bulk cervical scrapings have revealed marked differences in the spectra of normal and malignant samples. Despite the presence of these differences, their precise origin is unknown. Although it appears intuitively reasonable that changes in the malignant cell per se give rise to the spectral abnormalities associated with cancer, no confirmation of this exists. Still further, it has been observed that in some malignant cervical samples, the cancerous cells constitute no more than 10% of the total number of epithelial cells; yet, their infrared spectra are no different from those with far greater percentages of malignant cells. Without intending to be bound by any particular theory of operation, four possible explanations for such an observation are presented, including: 1) the changes in the cancer cell are so strong that they dominate the spectral contribution of the remaining 90+% of the cells, 2) the spectral changes originate from another type of cell, 3) cells not identifiable morphologically as malignant by Pap smear have already undergone the same or similar chemical changes as the malignant cell and therefore, together with the bone fide malignant cells constitute the majority of abnormal cells, and/or 4) cancer cells secrete chemicals that absorb strongly in the mid-infrared region and it is these chemicals that contribute to the spectral changes.

To address some of these issues, the present invention provides a novel method for the acquisition of spectra from cervical scrapings on a cell by cell basis.

4.1 Materials and Methods

Cells were fixed on a custom made ZnS (Cleartran) microscope slide and examined unstained under a Bio-Rad FT-IR UMA-500 microscope linked to a FTS 165 spectrometer. The aperture was adjusted to the size of individual cells and 500 spectra were co-added at a resolution of 8 cm$^{-1}$. Spectra were analyzed in the mid-IR range (950–3000 cm$^{-1}$). Zinc sulfide was chosen as the matrix for the support of the cells for three reasons. It provided a clear support for viewing the cells under a conventional microscope and an IR microscope. Second, the material was resistant to a number of chemicals including the stains used in Pap smears. Third, the material was well suited for the acquisition of spectra in the IR regions of interest.

(a) Preprocessing of Cervical Specimens

Cervical scrapings were collected by the standard brushing procedure. Exfoliated cells from each brush were gently shaken in vials which contained preservative solution (Preserv Cyt, CYTYC Corporation, Marlborough, Mass.). The preservative solution maintained the integrity of the exfoliated cells during transport and storage, and also served to lyse the red blood cells in the cervical scrapings. Vials containing the exfoliated cells were then treated with a CYTYC THIN PREP PROCESSOR®. The processor filtered out the mucus and non-diagnostic debris, and spread the cells in a uniform layer on the ZnS slides. In this manner, it is possible to selectively remove the majority of interfering materials from cervical scraping and obtain a uniform layer of cells while preserving the diagnostically important features of the cells. Infrared microspectroscopy was performed on unstained exfoliated cells which were recorded for their position by a cellfinder. Thereafter the slides were stained by the Papanicolaou stain, and were cytologically examined. The results of spectroscopy were then correlated with the cytological findings.

4.2 Results

Figure 5:
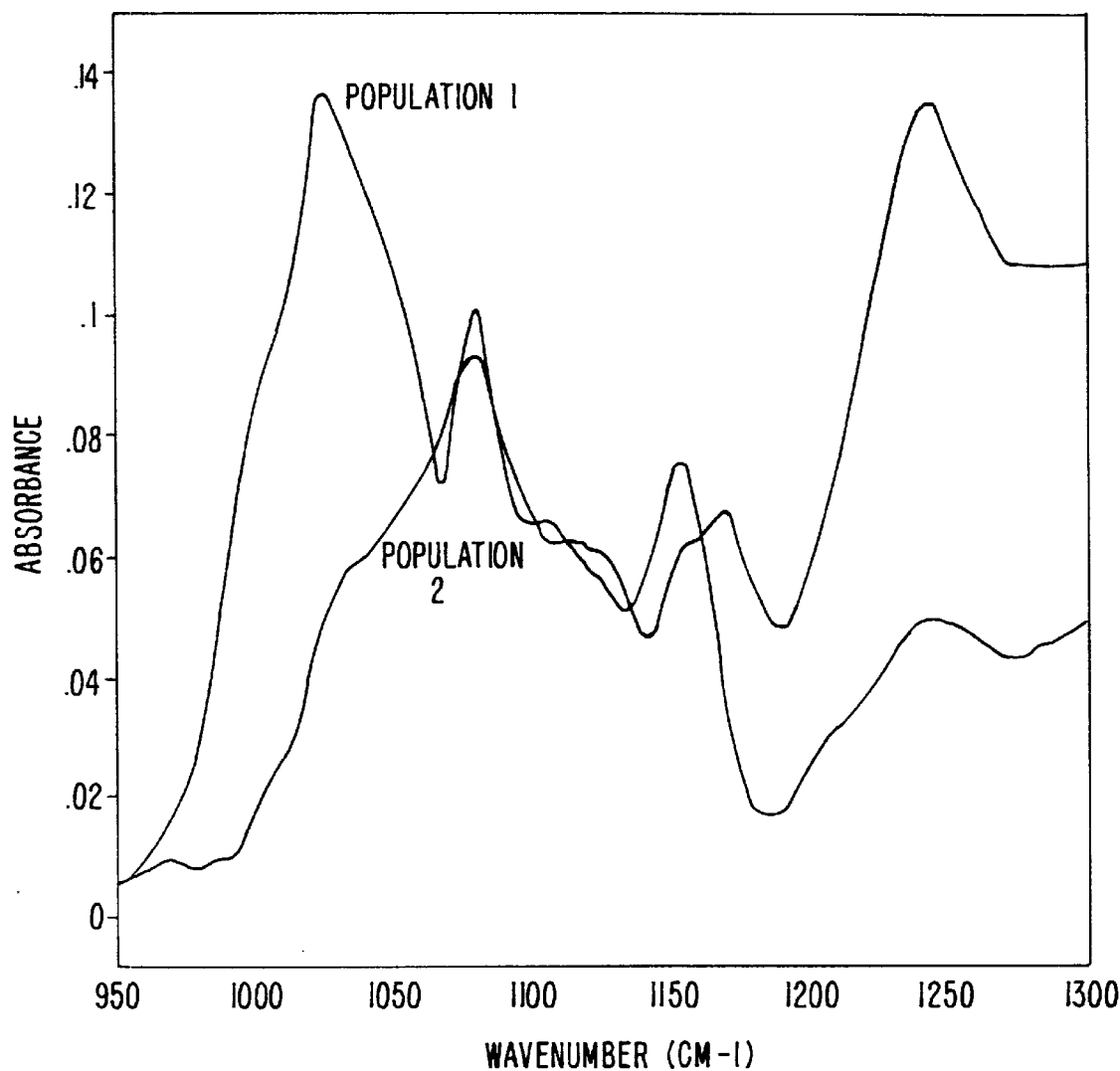
FIG. 5 shows the mid-infrared spectrum (from 950 $cm^{-1}$–1300 $cm^{-1}$) of two populations of squamous epithelial cells.
Figure 6:
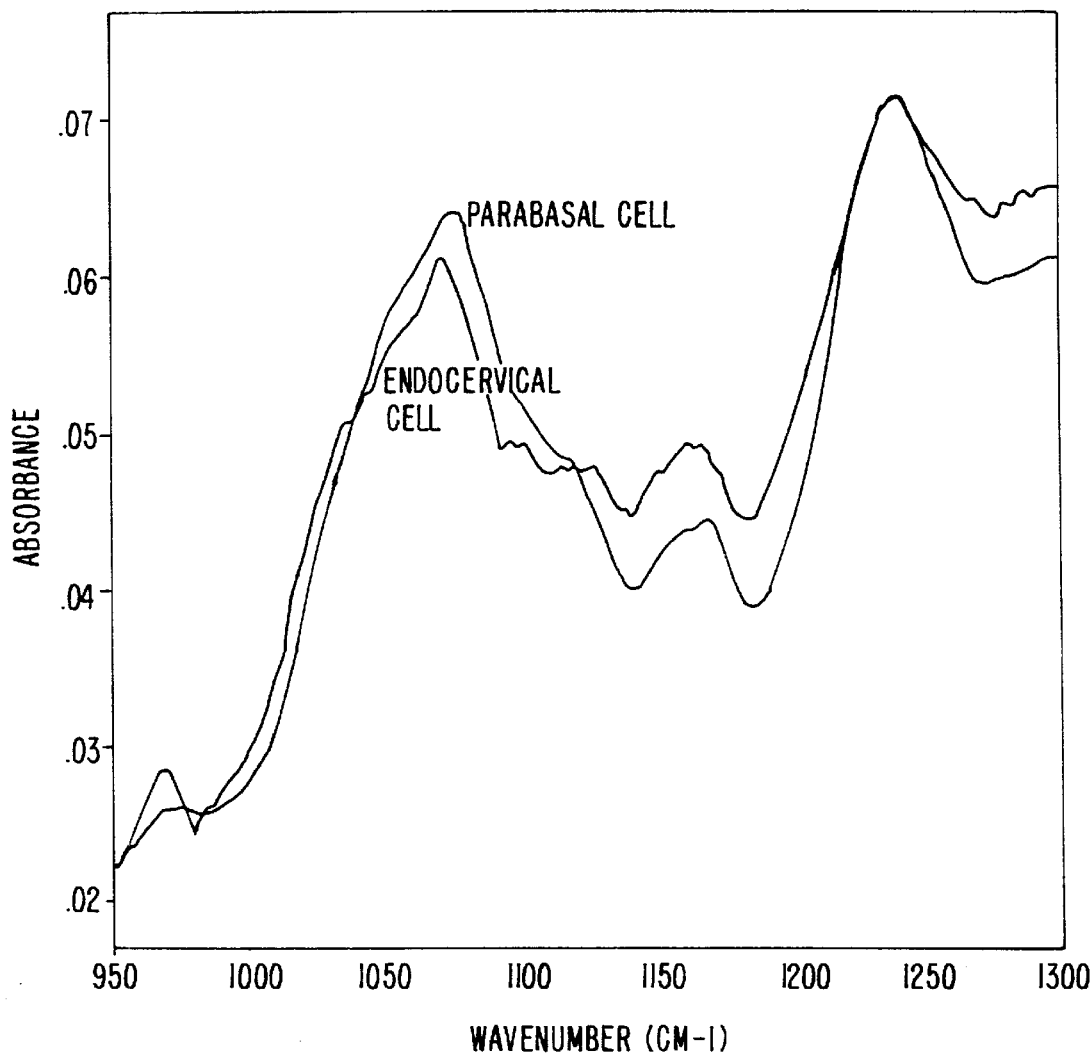
FIG. 6 shows a comparison of the mid-infrared spectra (from 950 $cm^{-1}$–1300 $cm^{-1}$) from parabasal cells and endocervical cells.

In the normal cervical scrapings four types of morphologically distinguishable cells were studied. These cells included the mature squamous epithelial cells, the intermediate squamous epithelial cells, parabasal cells and endocervical cells. Two different spectra were typically observed for the normal squamous epithelial cells. One spectrum appeared identical to the spectra for the normal cervical scrapings (FIG. 1), and the other appeared with a significantly diminished band at 1025 cm$^{-1}$. FIG. 5 shows the spectra of the two squamous cells. Squamous cells that had the typical spectrum of normal cells are referred to as Population 1, and those that lacked the 1025 cm$^{-1}$ band characteristic for glycogen are referred to as Population 2. The parabasal cells which are normally found in abundance in the cervical scrapings of menopausal patients with estrogen deficiency (e.g. a condition referred to as atrophic) exhibited spectra resembling the spectrum observed in malignant scrapings (FIG. 2, see also Wong, et al., *Proc. Natl. Acad. Sci. USA* 87:8140–8145 (1991)). This finding supported the PCA analysis in EXAMPLE 1 which found that highly significant frequencies of prediction as malignant are associated with Pap smears identified with "atrophic pattern" (e.g., contingency table, Table 4 code t $\chi^2$=13.7 p<0.001). While the spectra of endocervical cells also exhibited a diminished peak at 1025 $cm^{-1}$, a strong band at the 1076 $cm^{-1}$ region was also observed. FIG. 6 provides a comparison of the spectra of parabasal cells and endocervical cells.

Figure 7:
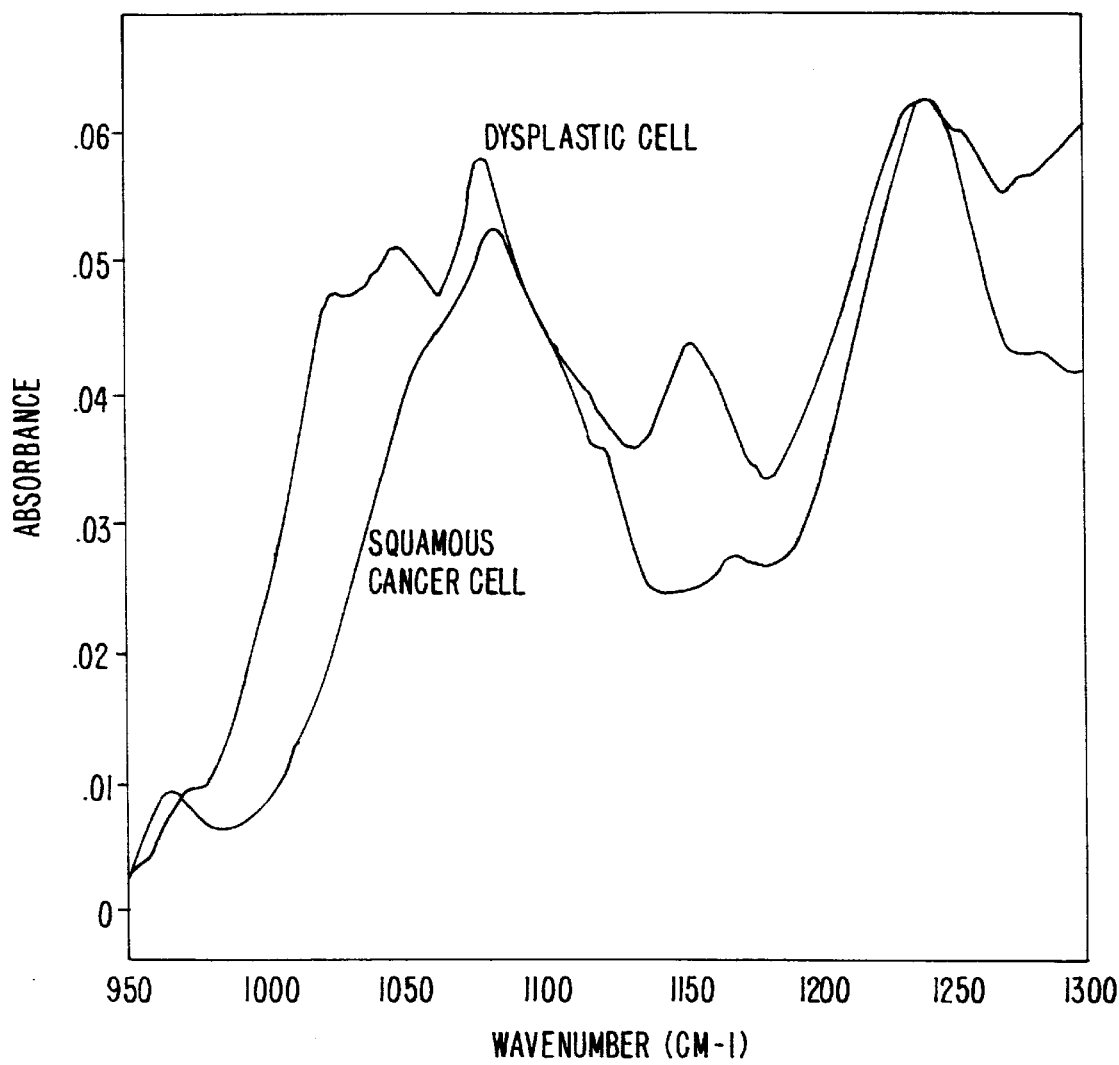
FIG. 7 shows a comparison of the mid-infrared spectra (from 950 $cm^{-1}$–1300 $cm^{-1}$) from a dysplastic cell and a squamous cancer cell.

The examination of malignant cells from patients with adenocarcinoma and squamous carcinoma of the cervix confirmed the spectral features reported by Wong, et al., ibid. All the malignant cells exhibited: 1) a prominent band at 970 $cm^{-1}$; and 2) a shift in the 1082 $cm^{-1}$ band to 1086 $cm^{-1}$. The loss in the band at 1025 $cm^{-1}$ was one of the main spectral features of the cancer cells. Microspectroscopic studies also showed that some cells diagnosed cytologically as dysplastic (CIN III) exhibited spectra intermediate in appearance between those of normal and malignant cells. FIG. 7 shows IR spectra from a malignant cell and a dysplastic cell with CIN III characteristics.

Although not wishing to be bound by any particular theory, a current working hypothesis for the mechanism which underlies the experimentally detected spectral changes is outlined below. It is currently thought that, upon undergoing an alteration from the normal phenotype to a disease or pre-disease phenotype, the cervical cell populations undergo a shift in the number of cells which exhibit spectra corresponding to Pattern I, Pattern II or a pattern intermediate between Pattern I and Pattern II. This shift is detectible in the absorption data derived from the cervical cell samples and may constitute the basis for distinguishing between the different cell types in a cervical cell sample.

The following examples will illustrate how single cell infrared spectroscopy based on the distribution of predicted scores generated by PLS or PCR can be used to distinguish normal cervical smears from smears with dysplasia and cancer.

Example 5

Example 5 shows the construction of a calibration/reference set of IR spectra derived from diagnostically normal cells which exhibit distinct spectral patterns (Pattern I, Pattern II).

5.1 Materials and Methods (a) Preprocessing of Cervical Scrapings

Cervical scrapings were collected and preserved as described in the examples above.

(b) Preparation and Classification of Cervical Smears

Two separate smears were prepared from each cell suspension with a CYTYC THIN PREP PROCESSOR® (CYTYC Corporation, Marlborough, Mass.). One smear was evaluated by conventional Papanicolaou staining, and the other by infrared microspectroscopy. On the basis of Pap evaluation, smears were classified in one of four diagnostic categories as follows: 1) the smears which were obtained from women with no present or past cervical disease, and which exhibited no morphological abnormality were labeled "normal"; 2) the smears which were acquired from patients with a history of dysplasia, and exhibited no morphological abnormality were labeled "normal-dysplasia"; 3) the smears which exhibited morphological changes associated with neoplasia, but showed no evidence of cancer were labeled "dysplasia"; and 4) those which displayed evidence of carcinoma in situ or cancer were labeled "malignant".

After diagnosing and classifying all specimens, 16 smears were selected for spectroscopic study. This selection was performed at random with the stipulation that within each diagnostic category four smears were to be selected. Of these samples, four smears were classified as "normal", four as "normal-dysplasia", four as "dysplasia", and four as "malignant".

(c) Infrared Spectroscopy

Cervical cells fixed on ZnS (Cleartran) microscope slides were examined unstained under a Bio-Rad FT-IR UMA-500 microscope linked to a Bio-Rad FTS 165 spectrometer.

The selection of cells for spectroscopy was performed at random and, since the morphological features of the unstained cells were barely detectable under low magnification, no cytological features influenced the selection process. The aperture was adjusted to the size of individual cells, and 700 scans were co-added at a resolution of 8 $cm^{-1}$. A single-beam spectrum of Cleartran window was used for a background reference with each spectrum. Unless otherwise indicated, from every smear approximately 100 spectra-each corresponding to a single cell-were collected.

(d) Chemometric Analysis

The PLS plus® computer program from Galactic Industries (Salem, N.H., U.S.A.) was used to evaluate the spectra of individual cells by different multivariate techniques such as Partial Least Squares (PLS) and Principle Component Regression (PCR). All spectra were normalized to have the minimum and the maximum absorbance set at 0.0 and 1.0, respectively. Normalization was confined to the region between 1000 $cm^{-1}$ and 3000 $cm^{-1}$, because most of the spectral changes between the normal and abnormal cervical specimens appeared in this region. Unless otherwise indicated, two spectral regions were utilized in the PCR or the PLS analysis. These regions included the frequency zones between 1200 $cm^{-1}$ to 1000 $cm^{-1}$, and 3000 $cm^{-1}$ to 2800 $cm^{-1}$. The calculation of F ratios, and the assignment of probability values to different spectra based on F ratio results, were performed by the method of Haaland and Thomas (*Anal. Chem.,* 60:1193 (1988); and *Anal. Chem.,* 60:1202 (1988)). All spectra with F-ratios corresponding to probability values greater than 0.99 were flagged out as outlier samples (PLSplus™ Add-on Application Software manual for GRAMS/386™ page 61, Galactic Industries Corporation, Salem, N.H.). Ranks for different calibration spectra were selected on the basis of the Prediction Residual Error Sum of Squares (PRESS), and comparison of the PRESS values with all ranks prior to the PRESS value at the minimum. The first rank that fell below the cut off probability level of 0.75 in the F test of significance was selected as the optimal rank for the analysis (PLSplus™ Add-on Application Software manual for GRAMS/386™ pages 55–56, Galactic Industries Corporation, Salem, N.H.).

(e) Analysis of Spectra by Visual Inspection

Inspection of the spectra of individual cells revealed that there existed primarily two spectroscopic patterns. Pattern I was characterized by a prominent band peaking at around 1025 $cm^{-1}$, and additional discrete bands peaking at around 1080 $cm^{-1}$, 1160 $cm^{-1}$, and a broad peak at around 1250 $cm^{-1}$. Pattern II was characterized by a significant reduction in the amplitude of the 1025 $cm^{-1}$ band, which had now lost its peak, and broadening of the 1080 $cm^{-1}$, and 1160 $cm^{-1}$ bands; the 1250 $cm^{-1}$ band maintained the features of the corresponding band in Pattern I (See FIG. 8). All other spectra appeared either atypical or as a hybrid of "Pattern I" and the "Pattern II" spectra.

(f) Calibration Spectra

While a combination of references can be used in conjunction with PCR, and/or PLS to differentiate between normal and abnormal cervical smears, because of space limitations, the examples here will be confined to only four sets of calibration spectra that were employed in the analysis.

5.2 Calibration Set I

Calibration Set I was comprised of two spectral patterns, each derived exclusively from a cytologically "normal" smear. One reference included a subset of normal cells that exhibited the Pattern I spectra, and the other reference was from a subset of normal cells that yielded the Pattern II spectra. Once the calibration set was prepared, the spectra exhibiting Pattern I were assigned a dummy variable of 0, and those exhibiting Pattern II were assigned a dummy cumulative percentage of the predicted scores within the x intervals, respectively.

Figure 10:
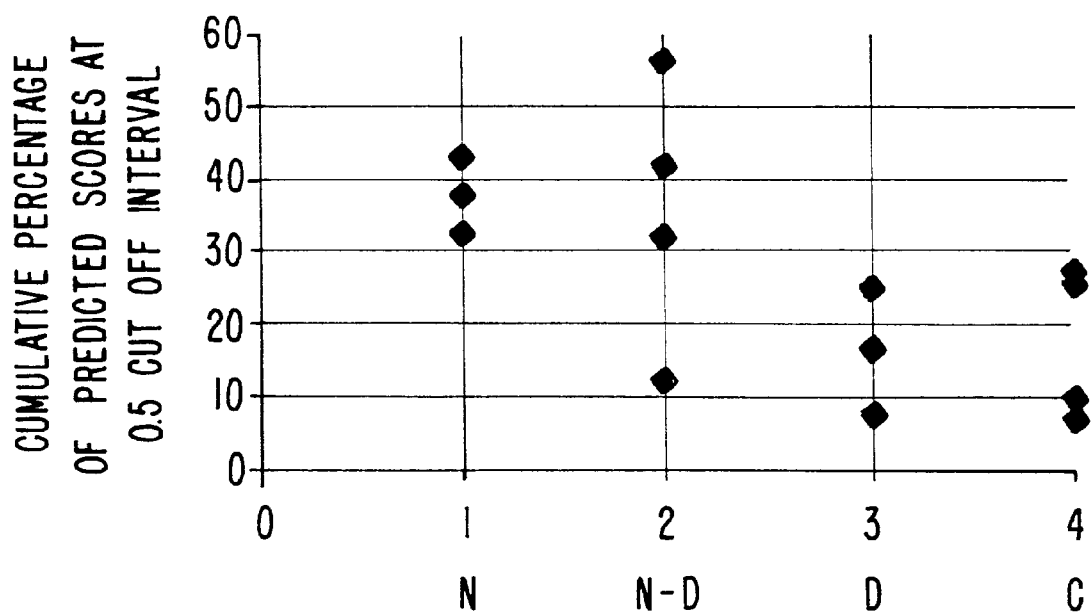
FIG. 10 summarizes the cumulative percentage of predicted scores at the 0.5 cut off interval based on histogram computations from all smears with calibration set I.

FIG. 10 summarizes the histogram computations at the 0.5 cut off interval based on the cumulative percentages of the predicted scores for all smears. The data clearly shows that at the 0.5 cut off interval there exists no overlap between the percent cumulative predicted scores from "normal" smears, and smears that were diagnosed with "dysplasia" or cancer. Some overlap, however, does exist between the percent cumulative predicted scores of the dysplasia and cancer smears with smears that were classified "normal-dysplasia". Included in FIG. 10 one also finds the mean, and the standard error of the mean for the predicted scores (i.e., in the four groups of smears) in each diagnostic category.

TABLE 8

DISTRIBUTION OF PREDICTED SCORES IN
CERVICAL SMEARS DIAGNOSED NORMAL OR NORMAL
DYSPLASIA USING CALIBRATION SET I

| Normal Specimen Interval | No. 1 Frequency | Cum % | No. 2 Frequency | Cum % | No. 3 Frequency | Cum % | No. 4 Frequency | Cum % |
| --- | --- | --- | --- | --- | --- | --- | --- | --- |
| −0.3 | 1 | 0.95 | 0 | 0.00 | 0 | 0 | 0 | 0 |
| −0.2 | 8 | 8.57 | 2 | 2.04 | 0 | 0 | 7 | 7 |
| −0.1 | 5 | 13.33 | 6 | 8.16 | 3 | 3 | 8 | 15 |
| 0 | 3 | 16.19 | 3 | 11.22 | 15 | 18 | 5 | 20 |
| 0.1 | 4 | 20.00 | 0 | 11.22 | 8 | 26 | 5 | 25 |
| 0.2 | 3 | 22.86 | 5 | 16.33 | 5 | 31 | 3 | 28 |
| 0.3 | 3 | 25.71 | 6 | 22.45 | 3 | 34 | 7 | 35 |
| 0.4 | 3 | 28.57 | 5 | 27.55 | 6 | 40 | 3 | 38 |
| 0.5 | 4 | 32.38 | 10 | 37.76 | 3 | 43 | 5 | 43 |
| 0.6 | 15 | 46.67 | 19 | 57.14 | 8 | 51 | 12 | 55 |
| 0.7 | 27 | 72.38 | 23 | 80.61 | 21 | 12 | 22 | 77 |
| 0.8 | 28 | 99.05 | 19 | 100.00 | 27 | 99 | 23 | 100 |
| 0.9 | 1 | 100.00 | | | 1 | 100 | | |
| Total | 105 | | 98 | | 100 | | 100 | |
| Normal-Dysplasia Specimen Interval | No. 1 Frequency | Cum % | No. 2 Frequency | Cum % | No. 3 Frequency | Cum % | No. 4 Frequency | Cum % |
| −0.1 | 4 | 4.08 | 8 | 8.12 | 2 | 2.04 | 5 | 5.26 |
| 0 | 1 | 5.10 | 10 | 16.33 | 7 | 9.18 | 15 | 21.05 |
| 0.1 | 0 | 5.10 | 8 | 24.49 | 4 | 13.27 | 7 | 28.42 |
| 0.2 | 4 | 9.18 | 10 | 34.69 | 3 | 16.33 | 4 | 32.63 |
| 0.3 | 0 | 9.18 | 8 | 42.86 | 4 | 20.41 | 3 | 35.79 |
| 0.4 | 2 | 11.22 | 8 | 51.02 | 6 | 26.53 | 1 | 36.84 |
| 0.5 | 1 | 12.24 | 5 | 56.12 | 5 | 31.63 | 4 | 41.05 |
| 0.6 | 3 | 15.31 | 8 | 64.29 | 11 | 42.86 | 3 | 44.21 |
| 0.7 | 17 | 32.85 | 15 | 79.59 | 19 | 62.24 | 13 | 57.69 |
| 0.8 | 65 | 98.98 | 20 | 100.00 | 37 | 100.00 | 36 | 95.79 |
| 0.9 | 1 | 100.00 | | | | | 4 | 100.00 |
| Total | 98 | | 98 | | 98 | | 95 | | variable of 1. A rank of 3 was selected for discrimination purposes. This rank was the first rank that fell below the cut off probability level of 0.75 in the F test of significance.

5.3 Results

Figure 9:
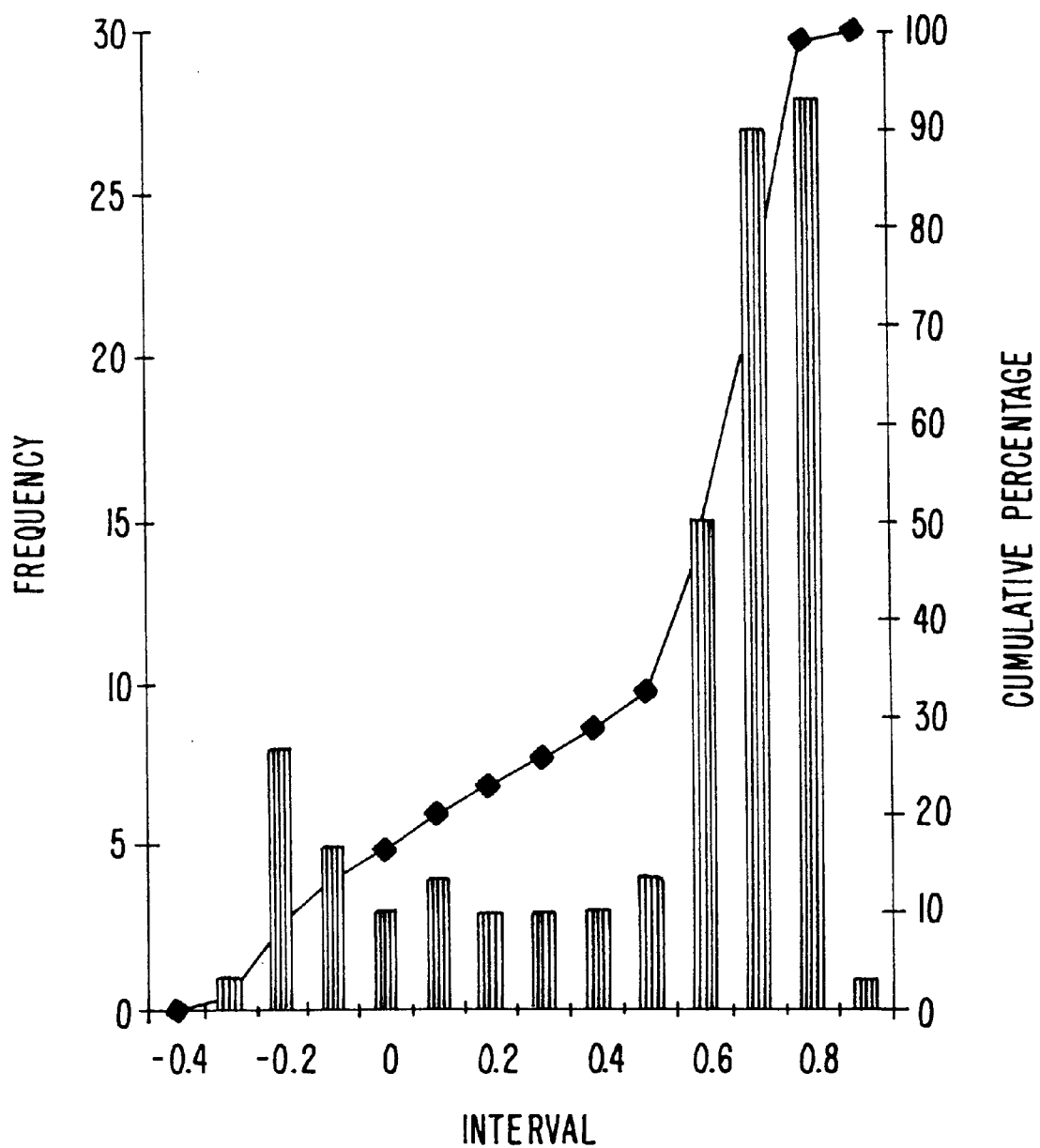
FIG. 9 shows a histogram representation of a set of predicted scores in a normal smear.

The spectra from different smears were stored in separate files and were evaluated by PLS and PCR. PLS and PCR generated a predicted score for each spectrum. The predicted scores from each smear were then sorted, and a histogram of their frequency distribution was constructed. Tables 8 and 9 show a series of such data. These data sets represent the distribution of the PLS predicted scores in each smear. FIG. 9 is a histogram representation of one of the data sets in Table 8. The x axis shows equally divided intervals, while a left and a right y axis indicate the frequency and the Statistical evaluation of the data clearly demonstrates significant differences in the mean score of normal specimens versus the smears with dysplasia and cancer. One explanation for this difference might be that compared to abnormal smears (e.g.,dysplasia and cancer), normal smears appear to have more cells exhibiting the Pattern I spectra, and fewer cells that yield the Pattern II spectra. This speculation is based on the observation that the mean predicted score of normal smears is closest to 0, whereas in abnormal specimens it is closest to 1 (e.g., recalling that the reference spectra associated with Patterns I and II were assigned dummy variables of 0 and 1 respectively). With the

TABLE 9

TABLE 2
DISTRIBUTION OF PREDICTED SCORES IN MALIGNANT AND DYSPLASTIC CERVICAL SMEARS USING CALIBRATION SET I

| Specimen | No. 1 | | No. 2 | | No. 3 | | No. 4 | |
|---|---|---|---|---|---|---|---|---|
| Interval | Frequency | Cum % | Frequency | Cum % | Frequency | Cum % | Frequency | Cum % |
| | | | | Cancer | | | | |
| −0.1 | 0 | 0.00 | 0 | 0 | 0 | 0.00 | 0 | 0 |
| 0 | 1 | 1.01 | 0 | 0 | 0 | 0.00 | 0 | 0 |
| 0.1 | 2 | 3.03 | 3 | 3 | 1 | 1.08 | 0 | 0 |
| 0.2 | 2 | 5.05 | 2 | 5 | 2 | 3.23 | 1 | 1 |
| 0.3 | 9 | 14.14 | 4 | 9 | 3 | 6.45 | 0 | 1 |
| 0.4 | 6 | 20.20 | 7 | 16 | 1 | 7.53 | 1 | 2 |
| 0.5 | 7 | 27.27 | 9 | 25 | 2 | 9.68 | 5 | 7 |
| 0.6 | 10 | 37.37 | 8 | 33 | 4 | 13.98 | 2 | 9 |
| 0.7 | 21 | 58.59 | 23 | 56 | 20 | 35.48 | 20 | 29 |
| 0.8 | 41 | 100.00 | 42 | 98 | 56 | 95.70 | 65 | 94 |
| 0.9 | | | 2 | 100 | 4 | 100.00 | 6 | 100 |
| Total | 99 | | 100 | | 93 | | 100 | |
| | | | | Dysplasia | | | | |
| −0.2 | 0 | 0.00 | 0 | 0.00 | 0 | 0.00 | 0 | 0.00 |
| −0.1 | 1 | 0.98 | 1 | 1.25 | 3 | 2.86 | 0 | 0.00 |
| 0 | 0 | 0.98 | 0 | 1.25 | 6 | 8.57 | 1 | 1.01 |
| 0.1 | 0 | 0.98 | 2 | 3.75 | 3 | 11.43 | 0 | 1.01 |
| 0.2 | 0 | 0.98 | 2 | 6.25 | 4 | 15.24 | 0 | 1.01 |
| 0.3 | 2 | 2.94 | 3 | 10.00 | 3 | 18.10 | 1 | 2.02 |
| 0.4 | 4 | 6.86 | 2 | 12.50 | 2 | 20.00 | 2 | 4.04 |
| 0.5 | 1 | 7.84 | 3 | 16.25 | 5 | 24.76 | 3 | 7.07 |
| 0.6 | 11 | 18.63 | 6 | 23.75 | 20 | 43.81 | 3 | 10.10 |
| 0.7 | 37 | 54.90 | 26 | 56.25 | 34 | 76.19 | 28 | 38.38 |
| 0.8 | 46 | 100.00 | 33 | 97.50 | 25 | 100.00 | 61 | 100.00 |
| 0.9 | | | 2 | 100.00 | 0 | | | |
| Total | 102 | | 80 | | 105 | | 99 | | progression of cervical disease from normal→normal dysplasia→dysplasia→cancer, one also notices an increase in the magnitude of spectral changes. For example, whereas the normal cervical smears yielded a mean predicted score of 0.443, the specimens with "normal dysplasia", dysplasia and cancer yielded increasing average scores of 0.499, 0.621 and 0.643, respectively. Analysis of the spectra by PCR revealed the same findings (data not shown).

Example 6

Example 6 demonstrates the construction of a calibration/reference set of IR spectra derived from normal cells exhibiting Pattern I spectra and dysplastic cells exhibiting Pattern II spectra.

6.1 Materials and Methods

The materials and methods used in Example 6 are substantially the same as those described in Example 5.

6.2 Calibration Set II

Calibration set II was comprised from two reference spectra. One reference included a subset of normal cells that exhibited the Pattern I spectra, and that were derived from smears which were diagnosed "normal". The second reference included a subset of cells that exhibited the Pattern II spectra, but which were derived from smears that were cytologically classified with "dysplasia". These reference spectra were selected at random and from different normal and dysplasia smears to ensure a thorough representation of the two spectral patterns. The spectra exhibiting Pattern I were assigned a dummy variable of 0, and the spectra exhibiting Pattern II were assigned a dummy variable of 1. Only one spectral region was utilized in the PCR or the PLS analysis. This frequency region included the zone between 1200 $cm^{-1}$ to 1000 $cm^{-1}$. For discrimination purposes, a rank of 6 was selected for the analysis.

6.3 Results

Tables 10 through 13 show a series of discrete data based on computations made by PLS using calibration set II as the reference spectra. Each data set represents one smear, and summarizes the distribution of predicted scores within that smear. Table 14 furnishes the mean and the standard deviation of the predicted scores that were computed for each smear. Statistical analysis of the data indicates a significant difference in the mean of the predicted scores of normal specimens relative to the specimens with dysplasia or cancer. A comparison of PLS results using calibration set II versus calibration set I also

TABLE 10

DISTRIBUTION OF PREDICTED SCORES IN MALIGNANT CERVICAL SMEARS USING CALIBRATION SET II

| | Sample No. 1 | | Sample No. 2 | | Sample No. 3 | | Sample No. 4 | |
|---|---|---|---|---|---|---|---|---|
| Interval | Frequency | Cum % | Frequency | Cum % | Frequency | Cum % | Frequency | Cum % |
| −0.1 | 0 | 0 | 0 | 0 | 1 | 1.086957 | 0 | 0 |
| 0 | 0 | 0 | 0 | 0 | 0 | 1.086957 | 0 | 0 |
| 0.1 | 6 | 6.185587 | 3 | 3.030303 | 1 | 2.173913 | 0 | 0 |
| 0.2 | 3 | 9.278351 | 2 | 5.050505 | 1 | 3.26087 | 0 | 0 |
| 0.3 | 9 | 18.5567 | 8 | 13.13131 | 0 | 3.26087 | 1 | 1.06383 |
| 0.4 | 4 | 22.68041 | 4 | 17.17172 | 1 | 4.347826 | 0 | 1.06383 |
| 0.5 | 4 | 26.80412 | 6 | 23.23232 | 4 | 8.695652 | 3 | 4.255319 |
| 0.6 | 6 | 32.98969 | 9 | 32.32323 | 1 | 9.782609 | 3 | 7.446809 |
| 0.7 | 16 | 49.48454 | 12 | 44.44444 | 6 | 16.30435 | 3 | 10.6383 |
| 0.8 | 30 | 80.41237 | 36 | 80.80808 | 14 | 31.52174 | 15 | 26.59574 |
| 0.9 | 12 | 92.78351 | 12 | 92.92929 | 31 | 65.21739 | 24 | 52.12766 |
| 1 | 1 | 93.81443 | 5 | 97.9798 | 17 | 83.69565 | 29 | 82.97872 |
| 1.1 | 4 | 97.93814 | 0 | 97.9798 | 10 | 94.56522 | 11 | 94.68085 |
| 1.2 | 1 | 98.96907 | 2 | 100 | 2 | 96.73913 | 5 | 100 |
| 1.3 | 1 | 100 | 0 | 100 | 1 | 97.82609 | 0 | 100 |
| 1.4 | 0 | 100 | 0 | 100 | 0 | 97.82609 | 0 | 100 |
| 1.5 | 0 | 100 | 0 | 100 | 1 | 98.91304 | 0 | 100 |
| 1.6 | 0 | 100 | 0 | 100 | 1 | 100 | 0 | 100 |
| Total | 97 | | 99 | | 92 | | 94 | |

TABLE 11

DISTRIBUTION OF PREDICTED SCORES IN DYSPLASTIC CERVICAL SMEARS USING CALIBRATION SET II

| | Sample No. 1 | | Sample No. 2 | | Sample No. 3 | | Sample No. 4 | |
|---|---|---|---|---|---|---|---|---|
| Interval | Frequency | Cum % | Frequency | Cum % | Frequency | Cum % | Frequency | Cum % |
| −0.2 | 0 | 0 | 0 | 0 | 0 | 0 | 1 | 1.111111 |
| −0.1 | 0 | 0 | 0 | 0 | 1 | 0.952381 | 0 | 1.111111 |
| 0 | 0 | 0 | 0 | 0 | 1 | 1.904762 | 0 | 1.111111 |
| 0.1 | 1 | 1 | 0 | 0 | 2 | 3.809524 | 0 | 1.111111 |
| 0.2 | 1 | 2 | 0 | 0 | 6 | 9.52381 | 0 | 1.111111 |
| 0.3 | 0 | 2 | 1 | 1.298701 | 5 | 14.28571 | 0 | 1.111111 |
| 0.4 | 0 | 2 | 2 | 3.896104 | 3 | 17.14286 | 2 | 3.333333 |
| 0.5 | 1 | 3 | 3 | 7.792208 | 5 | 21.90476 | 1 | 4.444444 |
| 0.6 | 4 | 7 | 7 | 16.88312 | 7 | 28.57143 | 2 | 6.666667 |
| 0.7 | 13 | 20 | 7 | 25.97403 | 14 | 41.90476 | 4 | 11.11111 |
| 0.8 | 41 | 61 | 23 | 55.84416 | 22 | 62.85714 | 10 | 22.22222 |
| 0.9 | 34 | 95 | 19 | 80.51948 | 28 | 89.52381 | 23 | 47.77778 |
| 1 | 4 | 99 | 9 | 92.20779 | 4 | 93.33333 | 26 | 76.66667 |
| 1.1 | 1 | 100 | 4 | 97.4026 | 3 | 96.19048 | 15 | 93.33333 |
| 1.2 | 0 | 100 | 1 | 98.7013 | 1 | 97.14286 | 4 | 97.77778 |
| 1.3 | 0 | 100 | 0 | 98.7013 | 2 | 99.04762 | 2 | 100 |
| 1.4 | 0 | 100 | 0 | 98.7013 | 0 | 99.04762 | 0 | 100 |
| 1.5 | 0 | 100 | 0 | 98.7013 | 0 | 99.04762 | 0 | 100 |
| 1.6 | 0 | 100 | 0 | 98.7013 | 1 | 100 | 0 | 100 |
| 1.7 | 0 | 100 | 0 | 98.7013 | 0 | 100 | 0 | 100 |
| 1.8 | 0 | 100 | 0 | 98.7013 | 0 | 100 | 0 | 100 |
| 1.9 | 0 | 100 | 0 | 98.7013 | 0 | 100 | 0 | 100 |
| 2 | 0 | 100 | 0 | 98.7013 | 0 | 100 | 0 | 100 |
| 2.1 | 0 | 100 | 1 | 100 | 0 | 100 | 0 | 100 |
| Total | 100 | | 77 | | 105 | | 90 | |

TABLE 12

DISTRIBUTION OF PREDICTED SCORES IN NORMAL CERVICAL SMEARS USING CALIBRATION SET II

| | Sample No. 1 | | Sample No. 2 | | Sample No. 3 | | Sample No. 4 | |
|---|---|---|---|---|---|---|---|---|
| Interval | Frequency | Cum % | Frequency | Cum % | Frequency | Cum % | Frequency | Cum % |
| −0.3 | 3 | 2.941176 | 4 | 4.123711 | 1 | 1.010101 | 1 | 1.041667 |

TABLE 12-continued

DISTRIBUTION OF PREDICTED SCORES IN NORMAL CERVICAL SMEARS
USING CALIBRATION SET II

|  | Sample No. 1 | | Sample No. 2 | | Sample No. 3 | | Sample No. 4 | |
|---|---|---|---|---|---|---|---|---|
| Interval | Frequency | Cum % | Frequency | Cum % | Frequency | Cum % | Frequency | Cum % |
| −0.2 | 2 | 4.901961 | 1 | 5.154639 | 3 | 4.040404 | 2 | 3.125 |
| −0.1 | 6 | 10.78431 | 5 | 10.30928 | 6 | 10.10101 | 6 | 9.375 |
| 0 | 9 | 19.60784 | 1 | 11.34021 | 7 | 17.17172 | 5 | 14.58333 |
| 0.1 | 3 | 22.54902 | 5 | 16.49485 | 9 | 26.26263 | 3 | 17.70833 |
| 0.2 | 3 | 25.4902 | 5 | 21.64948 | 8 | 34.34343 | 5 | 22.91667 |
| 0.3 | 1 | 26.47059 | 6 | 27.83505 | 10 | 44.44444 | 9 | 32.29167 |
| 0.4 | 2 | 28.43137 | 3 | 30.92784 | 3 | 47.47475 | 5 | 37.5 |
| 0.5 | 5 | 33.33333 | 5 | 36.08247 | 4 | 51.51515 | 9 | 46.875 |
| 0.6 | 5 | 38.23529 | 26 | 62.8866 | 5 | 56.56566 | 8 | 55.20833 |
| 0.7 | 22 | 59.80392 | 22 | 85.56701 | 9 | 65.65657 | 22 | 78.125 |
| 0.8 | 20 | 79.41176 | 7 | 92.78351 | 26 | 91.91919 | 17 | 95.83333 |
| 0.9 | 18 | 97.05882 | 4 | 96.90722 | 6 | 97.9798 | 2 | 97.91667 |
| 1 | 3 | 100 | 3 | 100 | 2 | 100 | 2 | 100 |
| Total | 102 | | 97 | | 99 | | 96 | |

TABLE 13

DISTRIBUTION OF PREDICTED SCORES IN NORMAL AND DYSPLASTIC CERVICAL SMEARS
USING CALIBRATION SET II

|  | Sample No. 1 | | Sample No. 2 | | Sample No. 3 | | Sample No. 4 | |
|---|---|---|---|---|---|---|---|---|
| Interval | Frequency | Cum % | Frequency | Cum % | Frequency | Cum % | Frequency | Cum % |
| −0.6 | 0 | 0 | 1 | 1.030928 | 0 | 0 | 0 | 0 |
| −0.5 | 0 | 0 | 1 | 2.061856 | 0 | 0 | 0 | 0 |
| −0.4 | 0 | 0 | 1 | 3.092784 | 1 | 1.041667 | 0 | 0 |
| −0.3 | 0 | 0 | 2 | 5.154639 | 2 | 3.125 | 1 | 1.086957 |
| −0.2 | 2 | 2.105263 | 4 | 9.278351 | 3 | 6.25 | 1 | 2.173913 |
| −0.1 | 2 | 4.210526 | 9 | 18.5567 | 4 | 10.41667 | 7 | 9.782609 |
| 0 | 2 | 6.315789 | 9 | 27.83505 | 2 | 12.5 | 8 | 18.47826 |
| 0.1 | 3 | 9.473684 | 12 | 40.20619 | 8 | 20.83333 | 6 | 25 |
| 0.2 | 1 | 10.52632 | 6 | 46.39175 | 7 | 28.125 | 4 | 29.34783 |
| 0.3 | 0 | 10.52632 | 9 | 55.6701 | 8 | 36.45833 | 6 | 35.86957 |
| 0.4 | 2 | 12.63158 | 11 | 67.01031 | 2 | 38.54167 | 1 | 38.95852 |
| 0.5 | 4 | 16.84211 | 4 | 71.13402 | 6 | 44.79167 | 5 | 42.3913 |
| 0.6 | 5 | 22.10526 | 8 | 79.38144 | 13 | 58.33333 | 1 | 43.47826 |
| 0.7 | 15 | 37.89474 | 11 | 90.72165 | 16 | 75 | 16 | 80.86957 |
| 0.8 | 38 | 77.89474 | 5 | 95.87629 | 11 | 86.45833 | 21 | 83.69565 |
| 0.9 | 14 | 92.63158 | 3 | 98.96907 | 9 | 95.83333 | 13 | 97.82609 |
| 1 | 5 | 97.89474 | 1 | 100 | 3 | 98.95833 | 2 | 100 |
| 1.1 | 2 | 100 | 0 | 100 | 1 | 100 | 0 | 100 |
| Total | 95 | | 97 | | 96 | | 92 | |

TABLE 14

STATISTICAL ANALYSIS OF PREDICTED SCORES GENERATED BY CALIBRATION SET II

| Sample Numbers | # of Spectra With Acceptable F-ratio | Average of Predicted Scores | Std. Deviation of Predicted Scores STDEV | Std. Error of the Mean SEM | Avg. of Means | STDEV of Means | SEM |
|---|---|---|---|---|---|---|---|
| NORMAL CERVICAL SAMPLES | | | | | | | |
| 1 | 102 | 0.5032 | 0.3742 | 0.037051 | 0.445558 | 0.042731 | 0.021366 |
| 2 | 97 | 0.44248 | 0.31467 | 0.03195 | | | |
| 3 | 99 | 0.40015 | 0.3587 | 0.036051 | | | |
| 4 | 96 | 0.4364 | 0.31748 | 0.032403 | | | |
| CERVICAL SMEARS WITH DYSPLASIA | | | | | | | |
| 1 | 100 | 0.75953 | 0.1262 | 0.01262 | 0.772033 | 0.08356 | 0.04178 |
| 2 | 77 | 0.779 | 0.22067 | 0.025148 | | | |
| 3 | 105 | 0.673 | 0.282 | 0.02752 | | | |
| 4 | 90 | 0.8766 | 0.2024 | 0.021335 | | | |

TABLE 14-continued

STATISTICAL ANALYSIS OF PREDICTED SCORES GENERATED BY CALIBRATION SET II

Figure 11:
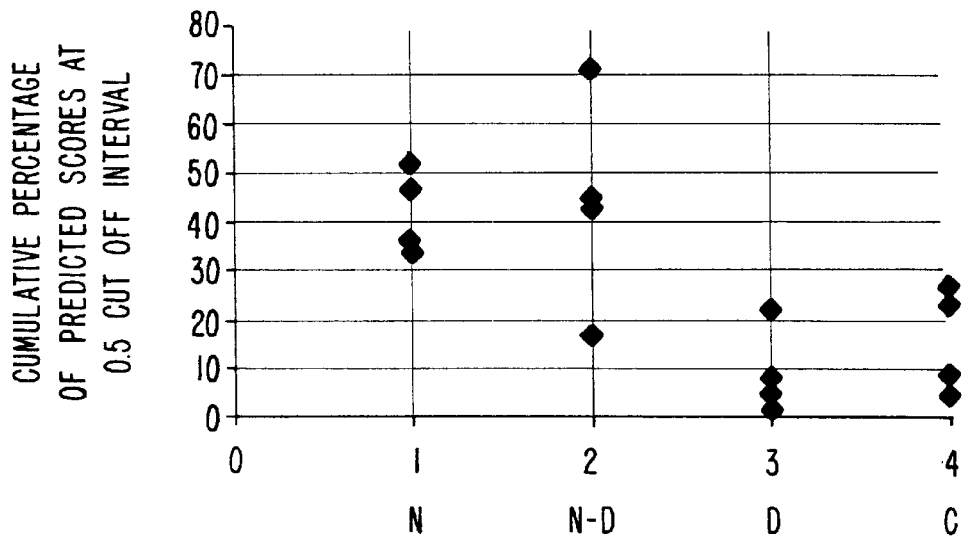
FIG. 11 summarizes the cumulative percentage of predicted scores at the 0.5 cut off interval based on histogram computations from all smears with calibration set II.

| Sample Numbers | # of Spectra With Acceptable F-ratio | Average of Predicted Scores | Std. Deviation of Predicted Scores STDEV | Std. Error of the Mean SEM | Avg. of Means | STDEV of Means | SEM |
|---|---|---|---|---|---|---|---|
| CERVICAL SMEARS WITH CANCER | | | | | | | |
| 1 | 97 | 0.6178 | 0.26742 | 0.027152 | 0.741433 | 0.130744 | 0.065372 |
| 2 | 99 | 0.64143 | 0.23425 | 0.023543 | | | |
| 3 | 92 | 0.831 | 0.233 | 0.024292 | | | |
| 4 | 94 | 0.8755 | 0.15946 | 0.016447 | | | |
| CERVICAL SMEARS WITH NORMAL DYSPLASIA | | | | | | | |
| 1 | 95 | 0.6463 | 0.28262 | 0.028996 | 0.444768 | 0.168378 | 0.084189 |
| 2 | 97 | 0.234746 | 0.35617 | 0.036164 | | | |
| 3 | 96 | 0.436906 | 0.355538 | 0.036287 | | | |
| 4 | 92 | 0.461121 | 0.361554 | 0.037695 | | | | revealed a wider spread in the means of the predicted scores of the normal cervical smears relative to the smears with dysplasia or cancer. While there are several possible explanations for this difference, we speculate that this change is brought about by subtle differences between the Pattern II spectra of cells in normal specimens, and of the Pattern II spectra of cells in the specimens with dysplasia. The progression of normal cells to dysplasia might be biochemically induced, and IR spectroscopy could be providing a window onto the results or origins of these biochemical changes. Additionally, as in the previous calibration, the results here indicate that normal cervical smears have a higher percentage of cells with the Pattern I spectra compared to the dysplasia smears where the Pattern II spectra predominate. The closeness to 0 in the mean of the predicted scores of normal smears, and to 1 of that of the abnormal smears supports this conclusion (e.g., the reference spectra associated with patterns I and II were assigned dummy variable values of 0 and 1, respectively). Finally, if one examines the cumulative predicted scores of the histogram results for all smears at the 0.5 cut off interval, it becomes evident that calibration set II, like calibration set I, clearly demarcates the normal smears from the smears with dysplasia and cancer (see FIG. 11).

The findings using PCR analysis were similar (data not shown).

Example 7

Example 7 illustrates a calibration/reference set composed of spectra from normal cells exhibiting Pattern I spectra and malignant cells with Pattern II spectra.

7.1 Materials and Methods

The materials and methods used in this example are substantially the same as those used in Example 5.

7.2 Calibration Set III

Calibration set III was comprised of two reference spectra. One reference spectrum included a subset of normal cells that exhibited the Pattern I spectra, and that were derived from the cytologically diagnosed smears labeled "normal". The second reference spectrum included a subset of cells that exhibited the Pattern II spectra, and which were derived from smears that were cytologically diagnosed as "malignant". These reference spectra were selected at random; each was from different normal and malignant smears, to ensure a thorough representation of the two spectral patterns. The spectra exhibiting Pattern I were assigned a dummy variable of 0, and the spectra exhibiting Pattern II were assigned a dummy variable of 1. For final analysis, a rank of 6 was selected for discrimination purposes.

7.3 Results

Figure 12:
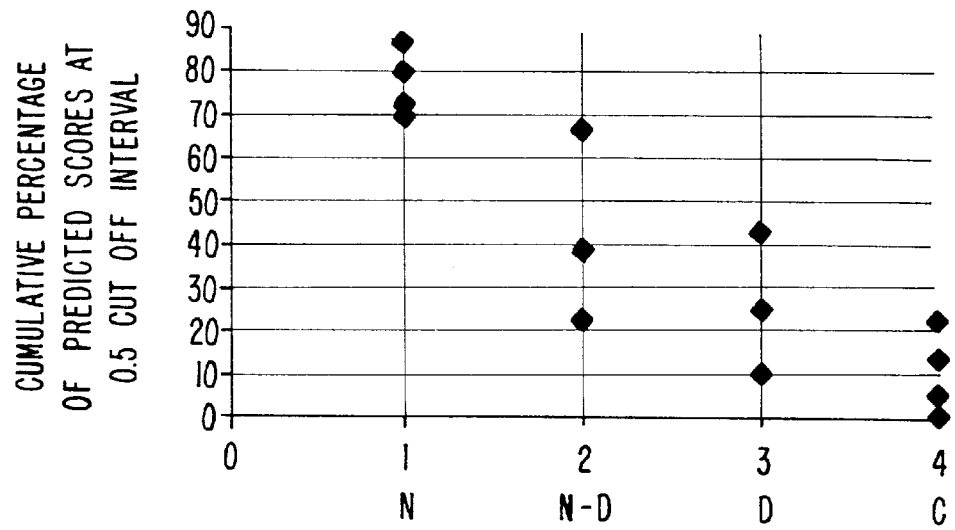
FIG. 12 summarizes the cumulative percentage of predicted scores at the 0.5 cut off interval based on histogram computations from all smears with calibration set III.

Calibration set III was employed in PLS analysis to compute predicted scores for all spectra. These predicted scores were then converted into a series of discrete data in a manner identical to the entries that were made earlier (See Tables 8, 9, and 11). FIG. 12 summarizes the histogram computations at the 0.5 cut off interval based on the cumulative percentages of the predicted scores for all smears. The data clearly shows that at the 0.5 cut off interval there exists no overlap between the percent cumulative predicted scores of "normal" smears, and the smears that were diagnosed with "dysplasia" and cancer. Also provided in FIG. 12 are the means and the standard deviations of the predicted scores for the four groups of smears. Close scrutiny of the data indicates that the choice of calibration affects the spread in the mean of the predicted scores of the various categories of smears. More importantly, the extent in the spread seems to be directly related to type of spectra in the calibration set, and the degree of abnormality of the cells from which the spectra were derived. Therefore, in using the spectra of cells from cancer smears, it was not surprising that the greatest spread in the mean of predicted scores was observed with data that was generated by calibration set III. Likewise, it was not unusual to discover that the spread in the means of the predicted scores for all groups of smears was greatest for data that was generated by calibration set II versus calibration set I. A possible explanation for this observation is that the difference in the means of the predicted scores is related primarily to the Pattern II spectra, and is brought about by the gradual conversion of normal cells to cancer, with dysplasia cells acting as an intermediary stage during this transformation process. Lastly, it is important to note, that in the transition from normalcy to malignancy there appears also a gradual shift in the percentage of cells exhibiting the Pattern I spectral features. For example, whereas the highest percentage of cells with Pattern I spectra are found in "normal" smears (FIG. 8), there is a lower percentage of these cells in "dysplasia" smears, and far lower in the "malignant" smears.

Example 8

Example 8 illustrates a calibration/reference set of IR spectra derived from normal cells with Pattern II spectra and malignant cells exhibiting Pattern II spectra.

8.1 Materials and Methods

The materials and methods used in this example are substantially the same as those used in Example 5.

8.2 Calibration Set IV

In an attempt to explore the variation in the Pattern II spectra of normal and cancer smears, a calibration reference consisting of only the Pattern II spectra was created. Those spectra that were derived from cytologically "normal" smears were assigned a dummy variable of 0, and those that were selected from cytologically "malignant" smears were assigned a dummy variable of 1. The rank of 6 was selected for discrimination purposes.

8.3 Results

Figure 13:
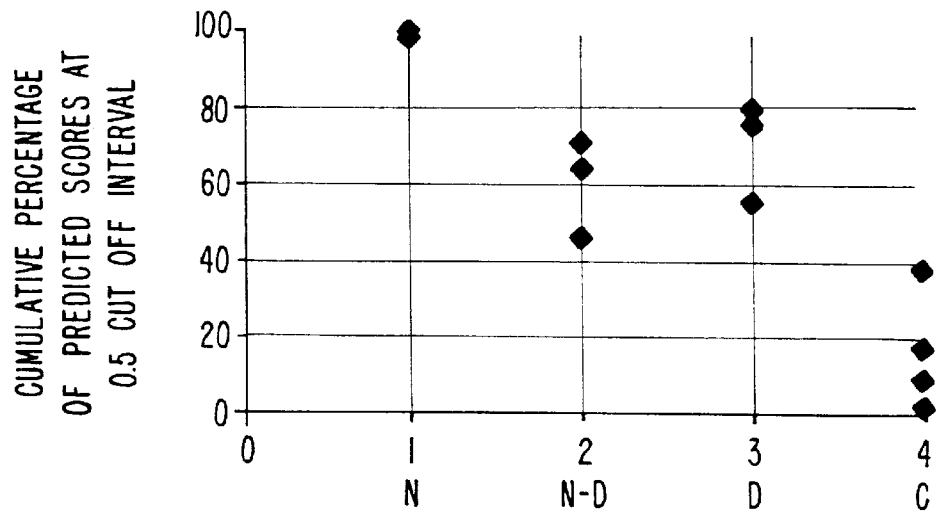
FIG. 13 summarizes the cumulative percentage of predicted scores at the 0.5 cut off interval based on histogram computations from all smears with calibration set IV.

Discrimination between the different categories of smear was most dramatic with this reference spectra. FIG. 13 summarizes the histogram computations at the 0.5 cut off interval for all smears. With the spectra of over 97% of the cells in the "normal" smears having a predicted score at or below the 0.5 cut off interval, PLS analysis using calibration set IV clearly demarcated the "normal" smears from all other smears. Also, as was intuitively anticipated, the highest percentage of spectra with predicted scores >0.5 were found in the group of smears that were labeled "malignant". Most interesting, however, was the percent difference at the 0.5 cut off interval in the predicted scores of the "normal" smears, and the cervical smears that were labeled "normal-dysplasia". For example, whereas 29% to 45% of the cells in the "normal dysplasia" smears had predictive scores greater than 0.5, no more than 2% of the cells in the normal smears were above the 0.5 cut off interval.

It will be apparent to one of skill in the art that the above described techniques will have application to absorption data acquired by spectroscopic techniques other than infrared spectroscopy. For example, differences in the nuclear magnetic resonance (NMR) or ultraviolet (UV) spectra of normal and aberrant cells can be used to characterize cell samples using the methods of the invention. The enumerated spectroscopic techniques are given by way of example and are not intended to limit the scope of the invention.

With the current techniques of cytological analysis (e.g., the Pap smear), it is impossible to distinguish between normal cervical smears that are derived from women with no prior history of dysplasia, and normal cervical smears that are derived from individuals with a past history of such a disease. That IR spectroscopy is distinguishing between these two groups of smears is therefore a vital finding. It is indeed probable that the observed difference in the percentages between the "normal" and the "normal-dysplasia" smears reflects significant chemical changes in the cervical cells that persist long after the dysplastic phenotype has reverted to normal, and that these changes can be detected by IR microspectroscopy. Further, it is conceivable that these chemical alterations in the cells have been initiated by the human papilloma virus. But regardless of the underlying mechanism, IR microspectroscopy as practiced here can indicate which women are at risk of cervical cancer. The infrared technique elucidated herein can also assess the degree of this risk, i.e., low versus high risk for cervical cancer.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications can be practiced within the scope of the appended claims.

What is claimed is:

1. An infrared imaging method for detecting chemical differences between a cell sample and a reference cell sample comprising:

(a) directing a beam of infrared light at said cell sample to produce absorption data for said cell sample;

(b) comparing said absorption data with a calibration/reference set of absorption spectra constructed by pixel-by-pixel analysis of infrared spectra acquired from at least one reference cell sample to generate comparison data;

(c) generating predicted scores for said comparison data utilizing multivariate analysis of said comparison data; and (d) creating frequency distribution profiles from said predicted scores, whereby said detection of chemical differences is made.

2. A method in accordance with claim 1, wherein the cell sample comprises exfoliated cervical cells.

3. A method in accordance with claim 1, wherein the beam of infrared light is of a frequency selected from a group consisting of from about 3000 $cm^{-1}$ to about 950 $cm^{-1}$ and from about 4000 $cm^{-1}$ to about 12000 $cm^{-1}$.

4. An infrared imaging method for distinguishing between normal, premalignant and malignant cells in a cell sample, said method comprising:

(a) directing a beam of infrared light at said cell sample to produce absorption data for said cell sample;

(b) comparing said absorption data with a calibration/reference set of infrared absorption spectra constructed by pixel-by-pixel analysis of infrared absorption spectra acquired from one or more cell types selected from the group consisting of cells cytologically determined to be normal, premalignant and malignant; to generate comparison data;

(c) generating predicted scores for said comparison data utilizing multivariate analysis of said comparison data; and (d) creating frequency distribution profiles from said predicted scores, whereby said normal, premalignant and malignant cells are distinguished.

5. A method in accordance with claim 4, wherein cells comprise exfoliated cervical cells.

* * * * *